US008318804B2

(12) United States Patent
Bisht et al.

(10) Patent No.: US 8,318,804 B2
(45) Date of Patent: Nov. 27, 2012

(54) ANTIVIRAL ACTIVITY OF CYCLOPENTENE NITRO-ESTER AND DERIVATIVES

(75) Inventors: Kirpal S. Bisht, Tampa, FL (US);
Alberto Van Olphen, Tampa, FL (US);
Pasha M. Khan, Tampa, FL (US);
Cynthia Bucher, Temple Terrace, FL (US)

(73) Assignee: University of South Florida, Tampa, FL (US)

( * ) Notice: Subject to any disclaimer, the term of this patent is extended or adjusted under 35 U.S.C. 154(b) by 317 days.

(21) Appl. No.: 12/797,290

(22) Filed: Jun. 9, 2010

(65) Prior Publication Data

US 2010/0249230 A1    Sep. 30, 2010

Related U.S. Application Data

(63) Continuation of application No. PCT/US2008/086155, filed on Dec. 10, 2008.

(60) Provisional application No. 61/012,611, filed on Dec. 10, 2007.

(51) Int. Cl.
*A01N 37/00* (2006.01)
*A01N 37/02* (2006.01)
*A61K 31/21* (2006.01)
*A61K 31/215* (2006.01)
*A61K 31/22* (2006.01)

(52) U.S. Cl. .......................... 514/506; 514/529; 514/546

(58) Field of Classification Search .................. 514/506, 514/529, 546
See application file for complete search history.

(56) References Cited

OTHER PUBLICATIONS

Hall et al., Are Amantadine and Rimantadine Effective in Healthy Adults with Acute Influenza?, Annals of Emergency Medicine, 2005, vol. 46, No. 3, pp. 292-293.
Keyser et al., Comparison of Central Nervous System Adverse Effects of Amantadine and Rimantadine Used as Sequential Prophylaxis of Influenza A in Elderly Nursing Home Patients, Arch. Intern. Med., 2000, vol. 160, pp. 1485-1488.
Chotpitayasunondh et al., Human Disease from Influenza A (H5N1), Thailand, 2004, Emerging Infectious Diseases, 2005, vol. 11, No. 2, pp. 201-209.
Bright et al., Incidence of Adamantane Resistance Among Influenza A (H3N2) Viruses Isolated Worldwide from 1994 to 2005: a Cause for Concern, Lancet, 2005, vol. 366, No. 11, pp. 1175-1181.
Bright et al., Adamantane Resistance Among Influenza A Viruses Isolated Early During the 2005-2006 Influenza Season in the United States, JAMA, 2006, vol. 295, No. 8, pp. 891-894.
Nicholson et al., Influenza, The Lancet, 2003, vol. 362, pp. 1733-1745.
Yen et al., Neuraminidase Inhibitor-Resistant Influenza Viruses May Differ Substantially in Fitness and Transmissibility, Antimicrobial Agents and Chemotherapy, 2005, vol. 49, No. 10, pp. 4075-4084.

Noah et al., A Cell-Based Luminescence Assay is Effective for High-Throughput Screening of Potential Influenza Antivirals, Antiviral Research, 2007, vol. 73, pp. 50-59.
Smee et al., Comparison of Colorimetric, Fluorometric, and Visual Methods for Determining Anti-Influenza (H1N1 and H3N2) Virus Activities and Toxicities of Compounds, Journal of Virological Methods, 2002, vol. 106, pp. 71-79.
Gebre-Mariam et al., Antiviral Activities of Some Ethiopian Medicinal Plants Used for the Treatment of Dermatological Disorders, Journal of Ethnopharmacology, 2006, vol. 104, pp. 182-187.
Trost et al., New Synthetic Reactions, Journal of the American Chemical Society, 1973, vol. 95, No. 1, pp. 292-294.
Trost et al., Asymmetric Transition-Metal-Catalyzed Allylic Alkylations: Applications in Total Synthesis, Chem. Rev., 2003, vol. 103, pp. 2921-2943.
Zeni et al., Synthesis of Heterocycles Via Palladium Pi-Olefin and Pi-Alkyne Chemistry, Chem. Rev., 2004, vol. 104, pp. 2285-2309.
Hayashi et al., Palladium-Catalyzed Asymmetric Intramolecular Allyation Forming Optically Active Vinylcyclopropane and Vinyldihydrofurans, Tetrahedron Letters, 1988, vol. 29, No. 6, pp. 669-672.
Yoshizaki et al., Palladium-Mediated Asymmetric Synthesis of Cis-3,6-Disubstituted Cyclohexenes. A Short Total Synthesis of Optically Active (+)-gamma-Lycorane, J. Org. Chem., 1995, vol. 60, pp. 2016-2021.
Trost et al., A Novel Pd-Catalyzed Cycloalkylation to Isoxazoline 2-Oxides. Application for the Asymmetric Synthesis of Carbanucleosides, J. Am. Chem. Soc., 1992, vol. 114, pp. 8745-8747.
Chen et al., New Cytotoxic Tetrahydrofuran- and Dihydrofuran-Type Lignans from the Stem of *Beilschmiedia tsangii*, Planta Med., 2006, vol. 72, pp. 351-357.
Faulkner, Marine Natural Products: Metabolites of Marine Algae and Herbivorous Marine Molluscs, J. Nat. Prod. Rep., 1984, vol. 1, pp. 251-280.
Usui et al., A New Microbial Metabolite, Sphydrofuran. II The Structure of Sphydrofuran, The Journal of Antibiotics, 1971, vol. XXIV, No. 2, pp. 93-106.
Sakai et al., Dysiherbaine: A New Neurotoxic Amino Acid from the Micronesian Marine Sponge Dysidea Herbacea, J. Am. Chem. Soc., 1997, vol. 119, pp. 4112-4116.
Encarnacion et al., Calafianin, a Bromotyrosine Derivative from the Marine Sponge *Aplysina gerardogreeni*, J. Nat. Prod., 2000, vol. 63, pp. 874-875.
Faulkner, Marine Natural Products, Nat. Prod. Rep., 2002, vol. 19, pp. 1-48.

(Continued)

*Primary Examiner* — Yong Chong
(74) *Attorney, Agent, or Firm* — Robert J. Varkonyi; Smith & Hopen, P.A.

(57) ABSTRACT

Disclosed is a method of synthesizing new optically pure heterocyclic compounds using Pd(0) catalyzed intramolecular cyclizations. Analogs of cyclopentanes, like isoxazoline-2-oxide and furan, with similar framework to the cyclopentanes act as anti-HIV and anticancer agents which opens a whole new field for application of these compounds. Starting from a meso-diol, optically pure compounds were prepared without utilizing chiral ligands at any stage of the synthesis. The stereochemical outcome of the product (>99% ee) was influenced by desymmetrization catalyzed by *Pseudomonas cepacia* lipase and the stereo selective nature of the palladium catalyzed transformations.

14 Claims, 10 Drawing Sheets

OTHER PUBLICATIONS

Benharref et al., Bromotyrosine Alkaloids from the Sponge *Pseudoceratina verrucosa*, J. Nat. Prod., 1996, vol. 59, pp. 177-180.

Nicholas et al., Novel Bromotyrosine Alkaloids: Inhibitors of Mycothiol S-Conjugate Amidase, Organic Letters, 2001, vol. 3, No. 10, pp. 1543-1545.

Groutas et al., Isoxazoline Derivatives as Potential Inhibitors of the Proteolytic Enzymes Human Leukocyte Elastase, Cathepsin G and Proteinase 3: a Structure-Activity Relationship Study, Bioorganic & Medicinal Chemistry, 1995, vol. 3, No. 2, pp. 125-128.

Lee et al., Single Organic Molecules Designed as Nanoscale Connectors: Fullerene Isoxazoline Derivatives, Bull. Korean Chem. Soc., 2004, vol. 25, No. 12, pp. 1850-1854.

Kunetsky et al., General Method for the Synthesis of Isoxazoline N-Oxides from Aliphatic Nitro Compounds, Synthesis, 2006, No. 13, pp. 2265-2270.

Kunetsky et al., New Approach for the Synthesis of Isoxazoline-N-Oxides, Organic Letters, 2003, vol. 5, No. 25, pp. 4907-4909.

Torssell, The Nitrile Oxides, Nitrones and Nitronates in Organic Synthesis, Feuer, H., Ed., VCH: Weinheim, 1988, pp. 55-74.

Tanimori et al., Simple Preparation of New Functionalized Furan Derivatives Via Sequential C-C and C-O Bond Formation Mediated by Palladium-Phosphine Catalyst, Synthesis, 2006, No. 5, pp. 865-869.

Crandall et al., A Synthesis of Homoallylic Alcohols, J. Org. Chem., 1968, vol. 33, No. 1, pp. 423-425.

Deardorff et al., A Highly Enantioselective Hydrolysis of CIS-3,5-Diacetoxycyclopent-1-ENE. An Enzymatic Preparation of 3(R)-Acetoxy-5(S)-Hydroxycyclopent-1-ENE, Tetrahedron Letters, 1986, vol. 27, No. 11, pp. 1255-1256.

Bisht et al., Enzyme-Mediated Regioselective Acylations of Sophorolipids, J. Org. Chem., 1999, vol. 64, pp. 780-789.

Garcia-Urdiales et al., Enantioselective Enzymatic Desymmetrizations in Organic Synthesis, Chem. Rev., 2005, vol. 105, pp. 313-354.

Johnson et al., Enzymatic Asymmetrization of Meso-2-Cycloalken-1,4-diols and Their Diacetates in Organic and Aqueous Media, Tetrahedron Letters, 1992, vol. 33, No. 48, pp. 7287-7290.

Carr et al., Enantioselective Synthesis of Imperanene Via Enzymatic Asymmetrization of an Intermediary 1,3-Diol, Organic Letters, 2004, vol. 6, No. 19, pp. 3297-3300.

Paquette et al., (4R)-(+)-tert-Butyldimethylsiloxy-2-Cyclopenten-1-One, Organic Synthesis, Coll., 1998, vol. 9, pp. 132, 1996, vol. 73, pp. 36.

Roy et al., 4'- and 1'-Methyl-Substituted 5'-Norcarbanucleosides, J. Org. Chem., 2003, vol. 68, pp. 9269-9273.

Fiaud et al., New Method for the Classification of Nucleophiles in the Palladium-Catalyzed Substitution of Allylic Acetates, J. Org. Chem., 1987, vol. 52, pp. 1907-1911.

Tsuji et al., Regioselective 1,4-Addiction of Nucleophiles to 1,3-Diene Monoepoxides Catalyzed by Palladium Complex, Tetrahedron Letters, 1981, vol. 22, No. 27, pp. 2575-2578.

Deardorff et al., A Palladium-Catalyzed Route to Mono- and Diprotected CIS-2-Cyclopentene-1,4-Diols, Tetrahedron Letters, 1985, vol. 26, No. 46, pp. 5615-5618.

Stange et al., Adverse Reactions to Amantadine Prophylaxis of Influenza in a Retirement Home, J. Am. Geriatr. Soc., 1991, vol. 39, No. 7, pp. 700-705.

Tsuji et al., Organic Syntheses by Means of Noble Metal Compounds XVII. Reaction of $\pi$-Allylpalladium Chloride with Nucleophiles, Tetrahedron Letters, 1965, vol. 49, pp. 4387-4388.

Nicolaou et al., Palladium-Catalyzed Cross-Coupling Reactions in Total Synthesis, Angew. Chem. Int. Ed., 2005, vol. 44, pp. 4442-4489.

Wright, Furans as Versatile Synthons for Target-Oriented and Diversity-Oriented Synthesis, Progress in Heterocyclic Chemistry, 2005, vol. 17, pp. 1-32.

Bindseil et al., Metabolic Products of Microorganisms, The Absolute Configuration of Sphydrofuran, a Widespread Metabolite from Streptomycetes, Helvetica Chimica Acta., 1991, vol. 74, pp. 1281-1286.

Siddiqi et al., Enantiospecific Synthesis of 5'-Noraristeromycin and Its 7-Deaza Derivative and a Formal Synthesis of (−)-5'-Homoaristeromycin, Nucleosides & Nucleotides, 1993, vol. 12, Nos. 3 & 4, pp. 267-278.

Whitney et al., Furoxans as Nitrile Oxide Precursors: Cycloaddition Reactions of BIS(Benzenesulfonyl) Furoxan, Tetrahedron Letters, 1981, vol. 22, No. 35, pp. 3371-3374.

Brunel et al., Experimental Evidence on the Existence of an exo-Pi-Allyl Complex Intermediate in the Pd0-Catalyzed Alkylation of a Bicyclic Allylic Diacetate with Stabilized Nucleophiles, Eur. J. Org. Chem., 2001, pp. 1009-1012.

Carr et al., Lipase-Catalyzed Resolution of 4-Aryl-Substituted Beta-Lactams: Effect of Substitution on the 4-Aryl Ring, Tetrahedron, 2003, vol. 59, pp. 9147-9160.

International Search Report for International Application No. PCT/US2008/086155 dated Jun. 1, 2009.

Shaker et al., Oral Antiplatelet Efficacy and Specificity of a Novel Nonpeptide Platelet GPIIb/IIIa Receptor Antagonist, DMP 802, Journal of Cardiovascular Pharmacology, 1998, vol. 32, No. 2, pp. 169-176.

Fattorussu et al., Aerothionin, a Tetrabromo-Compound from *Aplysina aerophoba* and *Verongia thiona*, Journal of the Chemical Scoeity, Chem. Communications, 1970, pp. 752-753.

Tsuji, Palladium Reagents and Catalysts, Chapter 4, Pd(0)-Catalyzed Reactions of Allylic Compounds Via Pi-Allylpalladium Complexes, Wiley, 2004, New York, New York, pp. 431-517.

Trost et al., Regiochemistry of the Cycloaddition of a Substituted Trimethylenemethanepalladium Complex, American Chemical Society, 1981, vol. 103, pp. 5972-5974.

Keinan et al., Regioselectivity in Organo-Transition-Metal Chemistry. A New Indicator Substrate for Classification of Nucleophiles, Journal of Organic Chemistry, 1983, Vol. 48, pp. 1769-1772.

A

B

| Compound | R₁ | R₂ | R₃ | Diastereomeric ratio | Yield |
|---|---|---|---|---|---|
| 17a | NO$_2$ | CO$_2$Et | H | 1.07:1 | 62 |
| 17b | NO$_2$ | CO$_2$Et | Me | 1.12:1 | 70 |
| 17c | NO$_2$ | CO$_2$Et | Bu | 1.11:1 | 72 |
| 17d | NO$_2$ | CO$_2$Et | C≡C-Ph | 1.13:1 | 60 |
| 17e | NO$_2$ | CO$_2$Et | C≡C-SiMe$_3$ | 1.15:1 | 68 |
| 17f | COMe | CO$_2$Et | H | 1.04:1 | 68 |
| 17g | COMe | CO$_2$Et | Me | 1.28:1 | 65 |
| 17h | COMe | CO$_2$Et | Bu | 1.19:1 | 70 |
| 17i | COPh | SO$_2$Ph | H | 1.07:1 | 68 |
| 17j | COPh | SO$_2$Ph | Me | 1.15:1 | 71 |
| 17k | COPh | SO$_2$Ph | Bu | 1.13:1 | 73 |
| 17l | COPh | SO$_2$Ph | C≡C-Ph | 1.06:1 | 61 |
| 17m | COPh | SO$_2$Ph | C≡C-SiMe$_3$ | 1.10:1 | 69 |
| 17n | CN | CO$_2$Et | H | 1.05:1 | 60 |
| 17o | CN | PhSO$_2$ | H | 1.23:1 | 68 |
| 17p | CO$_2$Me | CO$_2$Me | H | – | 73 |

| Compound | R1 | R2 | R3 | Yield[a] | $[\alpha]_D^{20}$ (CH$_2$C$_2$) |
|---|---|---|---|---|---|
| 19a | — | — | H | 85 | -95.2 |
| 19b | — | — | Me | 64 | -90.4 |
| 19c | — | — | Bu | 70 | -88.3 |
| 19d | — | — | C≡C–Ph | 63 | -182.3 |
| 19e | — | — | C≡C–SiMe$_3$ | 67 | -177.2 |
| 19f | Me | CO$_2$Et | H | 85 | -77.8 |
| 19g | Me | CO$_2$Et | Me | 57 | -148.1 |
| 19h | Me | CO$_2$Et | Bu | 55 | -258.8 |
| 19i | Ph | SO$_2$Ph | H | >98 | -20.0 |
| 19j | Ph | SO$_2$Ph | Me | 59 | -16.7 |
| 19k | Ph | SO$_2$Ph | Bu | 62 | -10.0 |
| 19l | Ph | SO$_2$Ph | C≡C–Ph | 65 | -15.0 |
| 19m | Ph | SO$_2$Ph | C≡C–SiMe$_3$ | 64 | -20.1 |
| 19n | CN | CO$_2$Et | H | —[b] | — |
| 19o | CN | SO$_2$Ph | H | —[b] | — |

[a] Product isolated after column chromatography.
[b] Starting material was recovered.

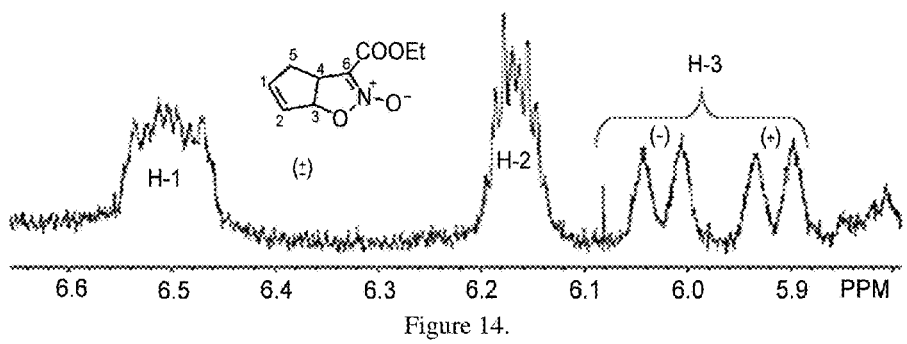
Figure 14.
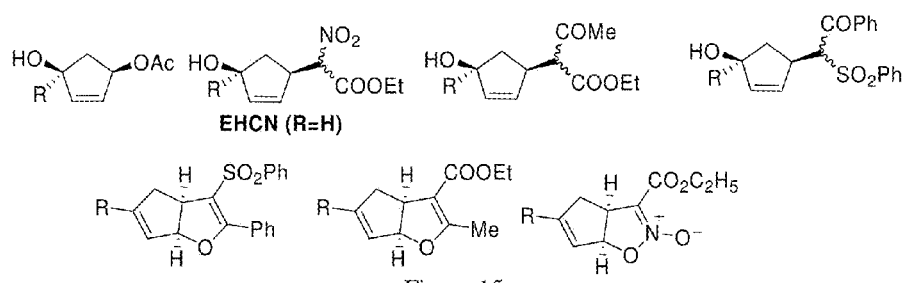
Figure 15.
| Well | 1 | 2 | 3 | 4 | 5 | 6 | 7 | 8 | 9 | 10 | 11 | 12 |
|------|------|--------|-------|--------|--------|-------|-------|--------|--------|--------|--------|-------|
| A | 2.69 | 1.57 | 2.94 | -4.52 | -4.27 | 37.49 | 13.75 | -11.60 | -40.06 | -40.06 | -38.19 | |
| B | -0.66 | 34.88 | 13.63 | 15.12 | 27.67 | 23.32 | 34.63 | 30.65 | -39.56 | -39.69 | -37.70 | |
| C | 14.87 | 2.07 | 29.16 | -13.84 | 16.24 | 12.26 | 26.93 | 10.27 | -39.31 | -38.94 | -38.94 | |
| D | 5.05 | 22.20 | 20.96 | 22.95 | -19.80 | -11.72 | 17.61 | 33.51 | -38.19 | -39.19 | -38.07 | -6.26 |
| E | 15.74 | 14.62 | 12.63 | 15.37 | 18.23 | 21.96 | 18.97 | 2.69 | -38.69 | -38.94 | -38.94 | -0.17 |
| F | -4.39 | 10.65 | 30.78 | 10.40 | 48.80 | 75.14 | 24.69 | 7.79 | -38.94 | -38.19 | -38.57 | |
| G | 0.46 | -32.23 | 1.20 | 19.59 | -36.08 | 20.84 | 3.44 | -1.66 | -38.44 | -39.19 | -38.44 | |
| H | 19.10 | 7.04 | 23.57 | 14.62 | 38.39 | 3.07 | -4.02 | -4.02 | -37.20 | -37.32 | -39.19 | |
Figure 16.

| Well | 1 | 2 | 3 | 4 | 5 | 6 | 7 | 8 | 9 | 10 | 11 | 12 |
|---|---|---|---|---|---|---|---|---|---|---|---|---|
| A | No | No | No | No | No | No | No | No | No | No | No | |
| B | No | No | No | No | No | No | No | No | No | No | No | |
| C | No | No | No | No | No | No | No | No | No | No | No | |
| D | No | No | No | No | No | No | No | No | No | No | No | No |
| E | No | No | No | No | No | No | No | No | No | No | No | No |
| F | No | No | No | No | No | Active | No | No | No | No | No | |
| G | No | No | No | No | No | No | No | No | No | No | No | |
| H | No | No | No | No | No | No | No | No | No | No | No | |

US 8,318,804 B2

ANTIVIRAL ACTIVITY OF CYCLOPENTENE NITRO-ESTER AND DERIVATIVES

CROSS REFERENCE TO RELATED APPLICATIONS

This application is a continuation of prior filed International Application, Ser. No. PCT/US2008/086155 filed Dec. 10, 2008, which claims priority to U.S. provisional patent application No. 61/012,611 filed Dec. 10, 2007 which is hereby incorporated by reference into this disclosure.

FIELD OF INVENTION

This invention relates to methods of treating and preventing viral diseases. Specifically, the invention provides for use of cyclic dienic ethers as antiviral compounds.

BACKGROUND OF THE INVENTION

The influenza virus belongs to the Orthomyxoviridae family and is a negative-sense, RNA virus with a segmented, single-stranded genome. Influenza is a viral disease spread initially from avian species and mutating into mammalian-infectious strains. The disease generally causes body aches, coughing, sneezing, fatigue, fever, headache, nausea, vomiting, and irritated eyes, skin, throat, and nose. The World Health Organization (WHO) estimates that 3 to 5 million people are infected each year, and as many as 500,000 people die from the complications of influenza infections in non-epidemic years and millions in epidemic years. The Center for Disease Control has found an average 5% to 20% of the U.S. population contracts influenze, with over 200,000 U.S. residents hospitalized and about 36,000 people dying from flu. Additional information provided by the WHO documents three influenza pandemics that occurred within the past century. The deadliest outbreak ever recorded (1918-19) killed about 40 million people worldwide, including about 650,000 in the United States. The economic impact caused by influenza due to decreased productivity and increased health care utilization is in the billions of dollars.

The viral nucleocapside is covered by a cell-derived envelop that contains three surface proteins: A trimeric hemagglutinin, and the tetrameric proteins Neuraminidase and M2. Two classes of antiviral drugs are currently in use in many countries around the world. The M2 ion channel blockers amantadine and rimantadine have been in use for a long time (Hall, M. and M. D. Brown. 2005. Evidence-based emergency medicine/systematic review abstract. Are amantadine and rimantadine effective in healthy adults with acute influenza? Ann. Emerg. Med. 46:292-293), however they are not well tolerated (Keyser, L. A., et al. 2000. Comparison of central nervous system adverse effects of amantadine and rimantadine used as sequential prophylaxis of influenza A in elderly nursing home patients. Arch. Intern. Med. 160:1485-1488; Stange, K. C., D. W. Little, and B. Blatnik. 1991.

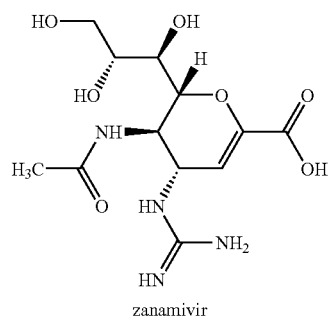

zanamivir

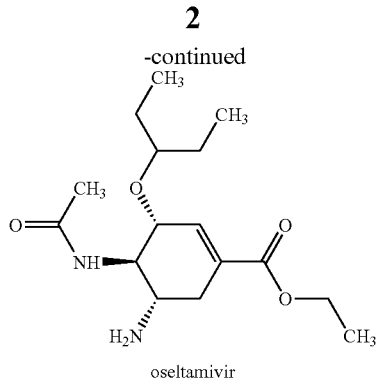

oseltamivir

Adverse reactions to amantadine prophylaxis of influenza in a retirement home. J Am. Geriatr. Soc. 39:700-705) and ineffective against the avian H5N1 virus. Neuraminidase-inhibitors (e.g. oseltamivir and zanamivir) are the only FDA-approved drugs available capable of reducing the risk of dying from H5N1 infection; however, the isolation of strains resistant to oseltamivir (Chotpitayasunondh, T. K. et al. 2005. Human disease from influenza A (H5N1), Thailand, 2004. Emerg. Infect. Dis. 11:201-209), and possible link to the appearance of neurological side-effects, emphasize the need for additional anti-influenza drugs. Ribavirin is a nucleoside mimetic anti-viral drug against DNA and RNA viruses, which interferes with duplication of viral genetic material. Ribavirin is approved only for use against chronic hepatitis C with hepatic damage in the United States, though Ribavirin exhibits an effect against influenza and is sold outside the U.S. as an anti-influenza medication.

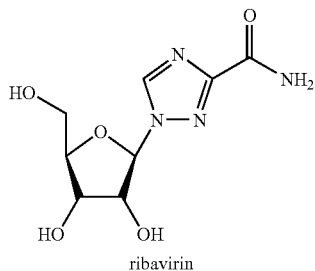

ribavirin

The appearance of drug-resistant isolates to adamantine (Bright, R. A., et al. 2005. Incidence of adamantane resistance among influenza A (H3N2) viruses isolated worldwide from 1994 to 2005: a cause for concern. Lancet 366:1175-1181; Bright, R. A., et al. 2006. Adamantane resistance among influenza A viruses isolated early during the 2005-2006 influenza season in the United States. JAMA 295:891-894) and neuraminidase inhibitors (Nicholson, K. G., et al. 2003. Influenza. The Lancet 362:1733-1745; Yen, H. L., et al. 2005. Neuraminidase Inhibitor-Resistant Influenza Viruses May Differ Substantially in Fitness and Transmissibility. Antimicrob. Agents Chemother. 49:4075-4084) further justifies the need to identify novel compounds with antiviral activity against influenza. Currently, scientists fear that the new avian influenza H5N1 could mutate into a strain that easily transmits from person to person, sparking a human influenza pandemic resulting in devastating human and economic consequences. Preparedness for a coming pandemic will require development of new vaccines and antiviral therapeutics. According to the WHO, since the initial outbreak in South East Asia in 1997 until Nov. 13th 2006, the H5N1 virus has thus far spread to at least ten countries and caused the death of 153 people and the mandatory slaughtering of millions of birds.

SUMMARY OF THE INVENTION

The syntheses of furan and isoxazoline-2-oxide analogs, seen in FIG. 1, were achieved by an intramolecular Pd(0) catalyzed cyclization and also involves enzymatic desymmetrization of meso starting materials. A cyclic dienic derivative was desymmetrization with a stereospecific hydrolase, like *Candida antarctica* lipase B. The desymmetrized compound is converted to a ketone, alkylating the ketone with a Pd(0) catalyst, and converting the alkylated ketone to an isoxazoline-2-oxide using a Pd(0) catalyst. The stereospecific heterocyclic compounds may alternatively be generated by cyclizing a starting cyclic dienic compound with a Pd catalyst in the presence of a base and desymmetrizing the resultant compound with the stereospecific hydrolase. Pd catalyzed cyclization reaction occurs in the presence of a base, such as sodium hydroxide, potassium carbonate, and potassium tert-butoxide.

The ketone is treated with alkyl lithium thereby generating cis diols. The cis diols are treated with acetic anhydride thereby generating monoacetate, followed by alkylating the monoacetate using a Pd catalyst, such as $Pd[P(C_6H_5)_3]_4$ and $Pd_2(C_{17}H_{14}O)_3$. The conversion of alkylated ketone to an isoxazoline-2-oxide further includes treating the monoacetate with potassium carbonate and palladium tetrakistriphenylphosphine.

These compounds were found to possess antiviral efficacy. Accordingly, the present disclosure provides methods of treating and preventing antiviral insult on a patient by administering a compound to an animal. In some embodiments, the compound used is a monocyclic cyclopentene compound. Contacting the compound to a cell infected with a single stranded RNA viral infection is shown to effectively treat the cell from the disease. The RNA viral infection may be a negative stranded RNA viral infection, such as type A or type B Orthomyxoviridae (influenza) infection.

Monocyclic cyclopentene compound, ethyl-(2R/S, 1'R, 4'S)-2-(4'-hydroxy-2'-cyclopenten-1'-yl)-2-nitroacetate (EHCN), has be found especially effective in treating and preventing Orthomyxoviridae (influenza) infection. In some embodiments, EHCN administered between 1.1 and 20 µg/ml, and may be specifically administered between 3.9 and 13.3 µg/ml. or more specifically at 5 µg/ml.

Also disclosed is a method of treating Orthomyxoviridae infection by contacting an infected cell with a therapeutically effective amount of a ethyl-(2R/S, 1'R,4'S)-2-(4'-hydroxy-2'-cyclopenten-1'-yl)-2-nitroacetate or a derivative. The Orthomyxoviridae infection may be either of type A or type B for specific treatments. Administration of EHCN has been found effective at between 1.1 and 20 µg/ml, and specifically between 3.9 and 13.3 µg/ml, or more specifically at 5 µg/ml.

BRIEF DESCRIPTION OF THE DRAWINGS

For a fuller understanding of the invention, reference should be made to the following detailed description, taken in connection with the accompanying drawings, in which:

FIG. 14 is a graph of $^1H$ NMR of racemic compound 19a, in the presence of (+)—$Eu(hfc)_3$. H-3 signals were used to calculate the % ee.

FIG. 15 depicts representative structures of Ethyl (2R/S, 1'R,4'S)-2-hydroxy-2'-cyclopenten-1'-yl)-2-nitroacetate and derivatives (EHCN). EHCN was synthesized using Pd(0) catalyzed alkylaion of a meso-diacetate using *Pseudomonas cepacia* lipase. The reaction occurs without the use of chiral ligands.

FIG. 16 is a cell viability was tested using a MIT cell assay for influenza infection. Wells A-C12 contained uninfected control, D-E12 contained 5 g/mL ribavirin, and F-H12 were the virus infected wells. Well F6 indicated a 75% protection from the selected influenza strain at 10 µg/mL.

DETAILED DESCRIPTION OF THE PREFERRED EMBODIMENT

Figures 2, 3:
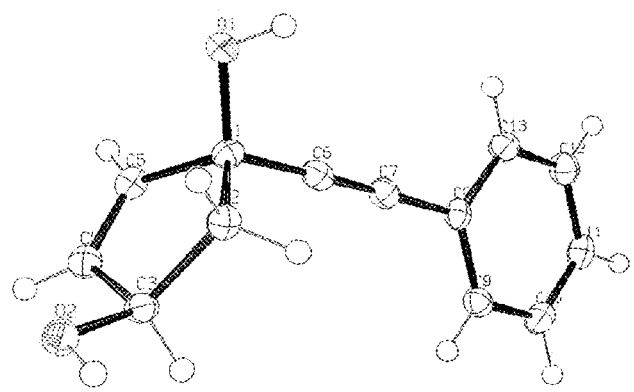
FIG. 2 is an ORTEP plot for X-ray structure of (1S, 4R)-1-Phenylethynyl-cyclopent-2-ene-1,4-diol (11).
FIG. 3 is a table of Pd(0) catalyzed alkylation, resulting in the formation of compounds 17a-p.

The syntheses of furan and isoxazoline-2-oxide analogs, seen in FIG. 2, were achieved by an intramolecular Pd(0) catalyzed cyclization and along with enzymatic desymmetrization of meso starting materials. These compounds were found to possess antiviral efficacy.

Thus, in accordance with this disclosure, a method is provided for treating and preventing viral infections using an effective dosage of a novel pharmaceutical composition. The treatment involves administering such pharmaceutical composition to a patient in need thereof, and may comprise combinations of said composition. In such combinations, the compounds of the disclosure and other active agents may be administered separately or in conjunction. In addition, the administration of one element may be prior to, concurrent to, or subsequent to the administration of other agent(s).

The "therapeutically effective amount" for purposes herein is thus determined by such considerations as are known in the art. A therapeutically effective amount of the novel compounds or any combination of the novel compound with or without additional compounds is that amount necessary to provide a therapeutically effective result in vivo. The amount of novel compounds with or without additional compounds must be effective to achieve a response, including but not limited to total prevention of (e.g., protection against) and to improved survival rate or more rapid recovery, or improvement or elimination of symptoms associated with viral diseases, including without limitation influenza, negatively stranded RNA viruses, and other indicators as are selected as appropriate measures by those skilled in the art. In accordance with the present invention, a suitable single dose size is a dose that is capable of preventing or alleviating (reducing or eliminating) a symptom in a patient when administered one or more times over a suitable time period. The "therapeutically effective amount" of a compound of the present invention will depend on the route of administration, type of patient being treated, and the physical characteristics of the patient. These factors and their relationship to dose are well known to one of skill in the medicinal art.

"Administration" or "administering" is used to describe the process in which compounds of the present invention, alone or in combination with other compounds, are delivered to a patient. The composition may be administered in various ways including oral, parenteral (referring to intravenous and intraarterial and other appropriate parenteral routes), intratheceally, intramuscularly, subcutaneously, colonically, rectally, and nasally, transcutaneuosly, among others. Each of these conditions may be readily treated using other administration routes of compounds of the present invention to treat a disease or condition. The dosing of compounds and compositions of the present invention to obtain a therapeutic or prophylactic effect is determined by the circumstances of the patient, as known in the art. The dosing of a patient herein may be accomplished through individual or unit doses of the compounds or compositions herein or by a combined or pre-packaged or pre-formulated dose of a compounds or compositions.

A pharmaceutical composition of the invention is formulated to be compatible with its intended route of administration. Examples of routes of administration include parenteral, e.g., intravenous, intradermal, subcutaneous, oral, inhalation, transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

The injectable solutions or suspensions may be formulated according to methods known in the art, using non-toxic, biologically compatible and/or parentally acceptable diluents or solvents such as mannitol, Ringer's solutions, sodium chloride solutions, or other suitable dispensing or wetting and suspending agents.

The pharmaceutical compositions of the subject invention can be formulated according to known methods for preparing pharmaceutically useful compositions. Furthermore, as used herein, the phrase "pharmaceutically acceptable carrier" means any of the standard pharmaceutically acceptable carriers. The pharmaceutically acceptable carrier can include diluents, adjutants, and vehicles, as well as implant carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. The pharmaceutical composition may be in the form of orally administrable suspensions or tablets, nasal sprays, sterile injectible preparations, such as sterile aqueous or oleageneous suspensions or suppositories. When administered orals or as a suspension, the composition is prepared according to techniques well known in the art of pharmaceutical formulation and may contain microcrystalline cellulose, dicalcium phosphate, starch, magnesium state, lactose and/or other excipients, binders, extenders, dilutants, lubricants, and flavoring known in the art. For example, *Remington's Pharmaceutical Sciences* (Martin E W [1995] Easton Pa., Mack Publishing Company, 19$^{th}$ ed.) describes formulations that can be used in connection with the subject invention.

The compounds of this disclosure may be administered orally to patient as a single dose or multiple, cumulative doses. It is understood that the specific dose will vary depending on the specific patient, such as age, sex, and diet. Other factors will also alter the dosage, such as the compound employed, metabolic stability of and duration of active complex in the patient, drug combination, rate of drug excretion, severity and type of condition to be remedied.

"Patient" is used to describe an animal, preferably a human, to whom treatment is administered, including prophylactic treatment with the compositions of the present invention.

The term "alkoxy" represents an alkyl group of indicated number of carbon atoms attached to the parent molecular moiety through an oxygen bridge. Examples of alkoxy groups include, for example, methoxy, ethoxy, propoxy and isopropoxy.

As used herein, the term "alkyl" includes those alkyl groups of a designed number of carbon atoms. Alkyl groups may be straight, or branched. Non-limiting examples of an "alkyl" include methyl, ethyl, propyl, isopropyl, butyl, iso-, sec- and tert-butyl, pentyl, hexyl, heptyl, 3-ethylbutyl, and the like.

As used herein, an "alcohol" is a compound on which a hydroxyl group is bound to a carbon atom of an alkyl or substituted alkyl group, which may act as a nucleophile as is known in the art, due to lone pairs of electrons on the oxygen of the hydroxyl group. Alcohols possessing short alkyl chains may be used as a protic solvent due to hydrogen bonding of its hydroxyl group, thereby promoting or enhancing solute solubility in water. The hydroxyl group also allows the alcohol to behave as a weak acid via deprotonation, or as a base. Oxidation of the alcohol results in an aldehyde, ketone or carboxylic acid, and can undergo nucleophilc substitution to form an ester compound. Alcohols may undergo E1 elimination reaction to produce alkenes.

The term "aryl" refers to an aromatic hydrocarbon ring system containing at least one aromatic ring. The aromatic ring may optionally be fused or otherwise attached to other aromatic hydrocarbon rings or non-aromatic hydrocarbon rings. Examples of aryl groups include, for example, phenyl, naphthyl, 1,2,3,4-tetrahydronaphthalene and biphenyl, phenyl, naphthyl, and anthracenyl. The term "heteroaryl" refers to an aromatic ring system containing at least one heteroatom selected from nitrogen, oxygen, and sulfur. The heteroaryl ring may be fused or otherwise attached to one or more heteroaryl rings, aromatic or non-aromatic hydrocarbon rings or heterocycloalkyl rings. Examples of heteroaryl groups include, for example, pyridine, furan, thienyl, 5,6,7,8-tetrahydroiso-quinoline and pyrimidine. Preferred examples of heteroaryl groups include thienyl, benzothienyl, pyridyl, quinolyl, pyrazolyl, pyrimidyl, imidazolyl, benzimidazolyl, furanyl, ben-zofuranyl, dibenzofuranyl, thiazolyl, benzothiazolyl, isox-azolyl, oxadiazolyl, isothiazolyl, benzisothiazolyl, triazolyl, pyrrolyl, indolyl, pyrazolyl, and benzopyrazolyl. [0219] When the either or both the A and B rings are substituted, the substitution may occur on either a carbon or on a heteroatom.

The term "cycloalkyl" refers to a cyclic hydrocarbon. Examples of cycloalkyl include cyclopropyl, cyclobutyl, cyclopentyl, cyclohexyl, cycloheptyl and cyclooctyl. The term "heterocycloalkyl," refers to a ring or ring system containing at least one heteroatom selected from nitrogen, oxygen, and sulfur, wherein said heteroatom is in a non-aromatic ring. The heterocycloalkyl ring is optionally fused to or otherwise attached to other heterocycloalkyl rings and/or non-aromatic hydrocarbon rings and/or phenyl rings. Preferred heterocycloalkyl groups have from 3 to 7 members. Examples of heterocycloalkyl groups include, for example, 1,2,3,4-tetrahydroisoquinolinyl, piperazinyl, morpholinyl, piperidinyl, tetrahydrofuranyl, pyrrolidinyl, pyridinonyl, and pyrazolidinyl. Preferred heterocycloalkyl groups include piperidinyl, piperazinyl, morpholinyl, pyrrolidinyl, pyridinonyl, dihydropyrrolidinyl, and pyrrolidinonyl.

The term "base" means a compound capable of acting as either an electron-pair donor or proton acceptor. In specific emobidments of the invention, the base is a Lewis base, thereby donating an electron-pair donor.

The compounds of this invention may contain one or more asymmetric carbon atoms, so that the compounds can exist in different stereoisomeric forms. These compounds can be, for example, racemates, chiral non-racemic or diastereomers. In these situations, the single enantiomers, i.e., optically active forms, can be obtained by asymmetric synthesis or by resolution of the racemates. Resolution of the racemates can be accomplished, for example, by conventional methods such as crystallization in the presence of a resolving agent; chromatography, using, for example a chiral HPLC column; or derivatizing the racemic mixture with a resolving reagent to generate diastereomers, separating the diastereomers via chromatography, and removing the resolving agent to generate the original compound in enantiomerically enriched form.

As used herein "lipase" is a hydrolase enzyme, either naturally derived or synthetic, that catalyzes the hydrolysis of ester bonds in water-insoluble, lipids. A lipase acts at a specific position on the glycerol backbone of lipid substrate As used herein "stereospecific" is used to describe the outcome of a chemical reaction including at least one chiral compound that yields a single stereoisomeric product from two or more stereoisomeric reactants. The resulting single stereoisomeric product possesses optical purity of at least 90%.

As used herein "heterocyclic compounds" are organic compounds containing at least one atom of carbon and at least one non-carbon element within a ring structure. The non-carbon element may be a nonmetal, such as sulfur, oxygen or nitrogen. Non-limiting examples include pyridine ($C_5H_5N$), pyrimidine ($C_4H_4N_2$) dioxane ($C_4H_8O_2$), quinoline ($C_9H_7N$), isoquinoline ($C_9H_7N$), pyrazine ($C_4H_4N_2$), pyridazine ($C_4H_4N_2$), furan ($C_4H_4O$), tetrahydrofuran ($C_4H_8O$), and indole ($C_8H_7N$).

As used herein, a "derivative" of a compound is any compound that shares functional efficacy and has or is derived from the same carbon framework. As used herein a derivative preferably is at least 90% structurally homologous.

Generation of Ethyl (2R/S,1'R,4'S)-2-(4'-hydroxy-2'-cyclopenten-1'-yl)-2-nitroacetate (EHCN) and derivatives.

Commercially available dicyclopentadiene was heated to 170° C. to obtain the monomer cyclopentadiene, which was oxidized using peracetic acid to its monoepoxide (Crandall, J. K.; et al. *J. Org. Chem.* 1968, 33, 423). The monoepoxide was subsequently treated with acetic anhydride in the presence of Pd(PPh$_3$)$_4$ to obtain the meso-3,5-diacetoxycyclopentene, see compound 6 in FIG. 1(b). The desymmetrization of meso-diacetate 6 with lipase to give the (+)-monoacetate, see compound 7 in FIG. 1(b), is the pivotal stereo-differentiation reaction.

To generate monoacetate 7, 10 g (0.054 mol) of meso-diacetate 6, was taken in a mixture of phosphate buffer (pH 7.0; 75 ml) and acetone (5 ml) in a round bottom flask. Lipase PS-30 (500 mg) was added while maintaining the pH of the reaction mixture at 7.0 using 1N NaOH solution. The reaction was stopped when no change in the pH of the reaction medium occurred. The conversion at this point was estimated to be ~60% by tlc with high enantiopurity (>97%). The reaction mixture was extracted with ethyl acetate (3×200 mL). The organic layer was dried over Na$_2$SO$_4$ and concentrated by rotoevaporation. The crude product was subjected to column chromatography over silica gel using ethylacetate: hexane (1:3) to isolate the monoacetate 7 as a white solid, mp 40-42° C.; $\alpha^D_{20}$ (CHCl$_3$)=+68.9; lit $\alpha^D_{20}$ (CHCl$_3$)=+69.6. A higher conversion could not be achieved even with extended reaction time, so the recovered diacetate was subjected to a second hydrolysis with the recovered enzyme to obtain enantiopure monoacetate 7 ($[\alpha]^{20}_D$+68.9 (CHCl$_3$); lit (Deardorff, D. R.; Matthews, A. J.; McMeekin, D. S.; Craney, C. L. *Tetrahedron Lett.* 1986, 27, 1255). ($[\alpha]^{20}_D$+69.6 (CHCl$_3$)) in total yield of 90%. The enantiopurity of monoacetate 7 was confirmed by GC analyses upon injecting racemic and enzymatically prepared monoacetate through a cyclodexB (30 m×0.25 mm, J&W scientific) chiral capillary column.

Figure 1:
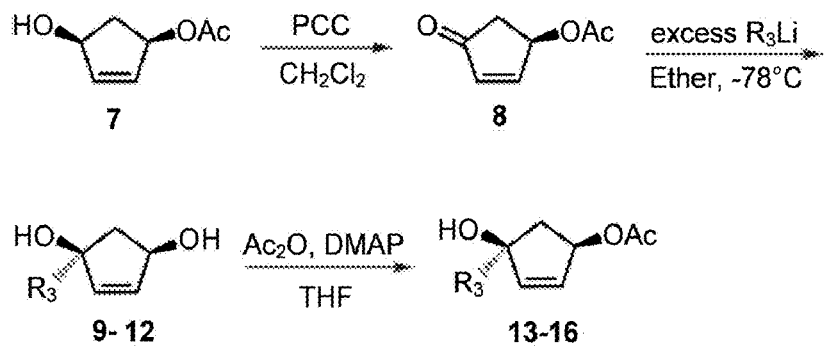
FIGS. 1(a)-(b) is an illustration of a chemical reaction showing synthesis of monoacetates 13-16. (A) Conversion of monoacetate to cis diols. (B) The full compound reaction from starting dicyclopentadience is shown.
Figure 1:
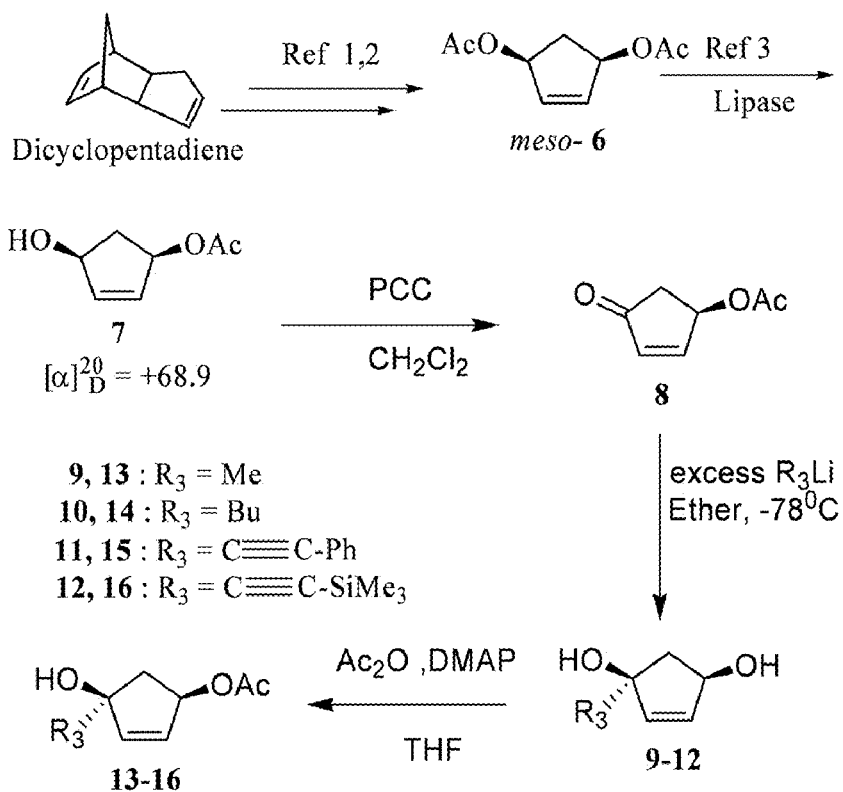

Monoacetate 7 was converted to ketone 8 using PCC (pyridinium chlorochromate) in the presence of sodium acetate in CH$_2$Cl$_2$, seen in FIG. 1(a). Ketone 8 was treated with alkyl lithium to generate cis-diols, 9-12 as the major products (>98%). To a solution of (R)-4-Acetoxy-2-cyclopenten-1-one 8 (200 mg, 1.428 mmol) in freshly distilled ether (15 ml) at −78° C. was added 1.6 M solution of methyl lithium in ether (3.57 ml, 5.712 mmol) under a nitrogen atmosphere. The reaction was allowed to stir for 1 h and was quenched using NH$_4$Cl solution. The product was purified by column chromatography using ethyl acetate: hexane (2:1) to afford compounds 9-12 (150 mg compound 9, yield=92%) as a viscous liquid with (+)-sign of optical rotation. Spectral data for compounds 10-12 were in complete agreement with the structures and for the known compound 9, $^1$H and $^{13}$C spectral data were identical to that reported in the literature (Roy, A.; Schneller, S. W. *J. Org. Chem.* 2003, 68, 9269).

Importantly, compound 11 produced colorless orthorhombic crystals and single crystal X-ray diffraction experimentation confirmed that the two hydroxyl groups are on the same side of the cyclopentene ring thus confirming the cis relationship, as seen in FIG. 2. The absolute stereochemistry of the molecule was also established as (1S,4R).

Figure 4:
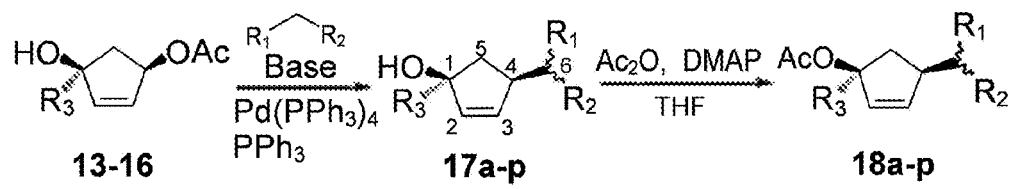
FIG. 4 is an illustration of a chemical reaction showing the synthesis of compounds 17a-p via Pd(0) catalysis.

To a solution of 9 (100 mg, 0.877 mmol) in dry THF (10 ml) at room temperature was added acetic anhydride (89 mg, 0.877 mmol), and catalytic amount of DMAP, seen in FIG. 1(a), (b). The reaction was allowed to stir for 3 h and then concentrated. The residue was taken in ethyl acetate (40 ml) and was treated twice with saturated sodium bicarbonate solution (20 ml), followed by brine (10 ml). The organic layer was dried over sodium sulfate and the resulting product 13 was purified by column chromatography using ethyl acetate: hexane (1:2) (80.25 mg, yield=58.77%). The monoacetates were then coupled to the soft nucleophiles generated from the active methylene compounds, seen in FIG. 3, via Pd catalyzed alkylation to give compounds 17a-p, seen in FIG. 4.

As evident from the mechanism for these alkylations, compounds 17a-o were expected to be a mixture of a pair of diastereomers at the site of the carbon-carbon bond formation (C-6). The diastereomeric ratio of 17a-o determined from integral value of the H-6, H-2, and H-3 resonances in their $^1$H spectra was calculated to be ~1:1, seen in FIG. 3. These pairs of diastereomers were inseparable on a chromatographic column and appeared as a single spot on a TLC plate. As the diastereotopic center (C-6) is prone to racemization (because of its proximity to the electron withdrawing groups) and is involved in generation of a carbanion in the following steps, no efforts were devoted to its resolution and the mixture was taken for further steps without separation. Treating a solution of 9 (100 mg, 0.877 mmol) with Pd, results in catalyzed alkylation of a 1, 4-adduct, and proceeds with high regio- and stereo-selectivity to give 17a-p. The stereochemistry of the Pd catalyzed allylation has been studied extensively and is known to proceed with retention of configuration via double inversion.

Acetates 18a-p were prepared by treating 17a-p with acetic anhydride in the presence of excess triethylamine and catalytic amount of DMAP. To a solution of 17a-h (100 mg, 0.465 mmol) in dry THF (10 ml) at room temperature was added acetic anhydride (51 mg, 0.5 mmol), and a catalytic amount of DMAP. The reaction was allowed to stir for 3 hours and then concentrated. The residue was taken up in ethyl acetate (40 ml) and extracted twice with saturated sodium bicarbonate solution (20 ml), followed by brine (10 ml). The organic layer was dried over sodium sulfate and the resulting product 18a-h (yield~92%) was obtained. Most tertiary acetates but 18b and 18d were unstable and not amenable to purification on chromatographic columns and hence, were subjected to palladium catalyzed alkylation without any further purification.

Compounds 17a-h may be alternatively generated by adding potassium carbonate (110 mg, 0.800 mmol) to a solution of ethyl nitroacetate (100 mg, 0.752 mmol) or ethylacetoacetate (98 mg, 0.752 mmol) in dry THF (10 ml) at room temperature under a nitrogen atmosphere. The reaction was allowed to stir for 20 minutes and Pd(PPh$_3$)$_4$ (43.4 mg, 0.037 mmol), PPh$_3$ (197 mg, 0.752 mmol), monoacetate 7 (106 mg, 0.752 mmol) dissolved in 5 ml THF was added to it. The reaction was allowed to stir at 40° C. for 12 h and then vacuum filtered through celite with subsequent concentration of the filtrate. The product was purified by column chromatography using ethyl acetate:hexane (1:2) to afford 17a-h (yield~62%). Acetic anhydride (51 mg, 0.5 mmol), and catalytic amount of DMAP is then added to a solution of 17a-h (100 mg, 0.465 mmol) in dry THF (10 ml) at room temperature. The reaction was allowed to stir for 3 hours and then concentrated. The residue was taken up in ethyl acetate (40 ml) and extracted twice with saturated sodium bicarbonate solution (20 ml), followed by brine (10 ml). The organic layer was dried over sodium sulfate and the resulting product 18a-h (yield~92%) was obtained.

Potassium carbonate (37.6 mg, 0.272 mmol) and Pd(PPh$_3$)$_4$ (15 mg, 0.013 mmol) were added to a solution of 18a (70 mg, 0.272 mmol) in dry THF (10 ml) at room temperature. The reaction was allowed to stir for 12 h at 60° C. and then vacuum filtered over celite with subsequent concentration of the filtrate. The product was purified by wet column chromatography using ethyl acetate: hexane (1:2) to afford 19a using column chromatography as a yellow viscous liquid (45 mg, yield=85%).

Figure 5:
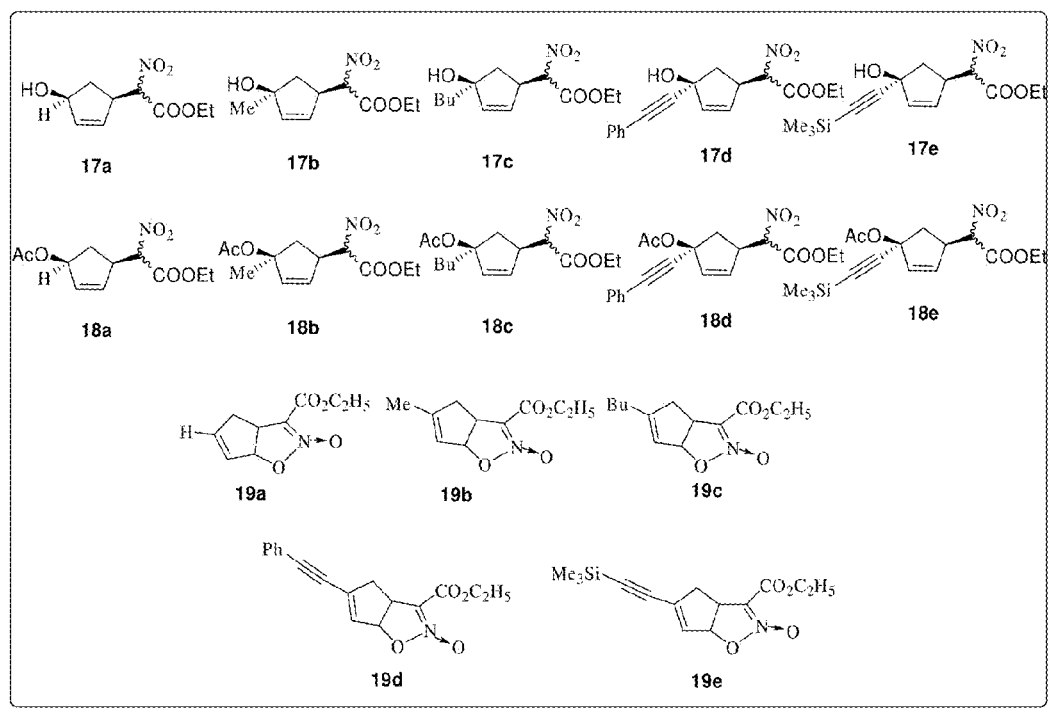
FIG. 5 depicts compounds synthesized using scheme 2, illustrated in FIGS. 1(a), (b) and 4.
Figure 6:
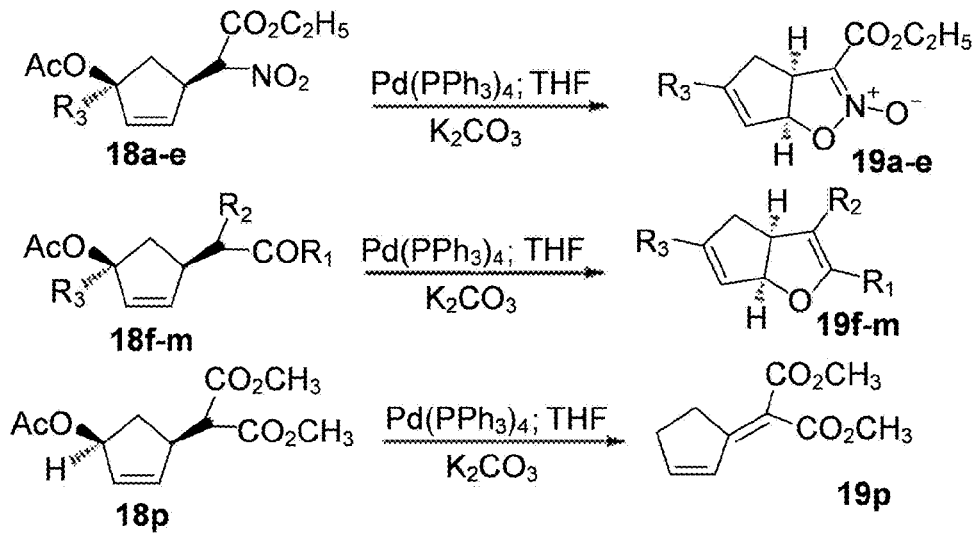
FIG. 6 is an illustration of a chemical reaction showing Pd(0) catalyzed intramolecular cyclization.
Figure 7:
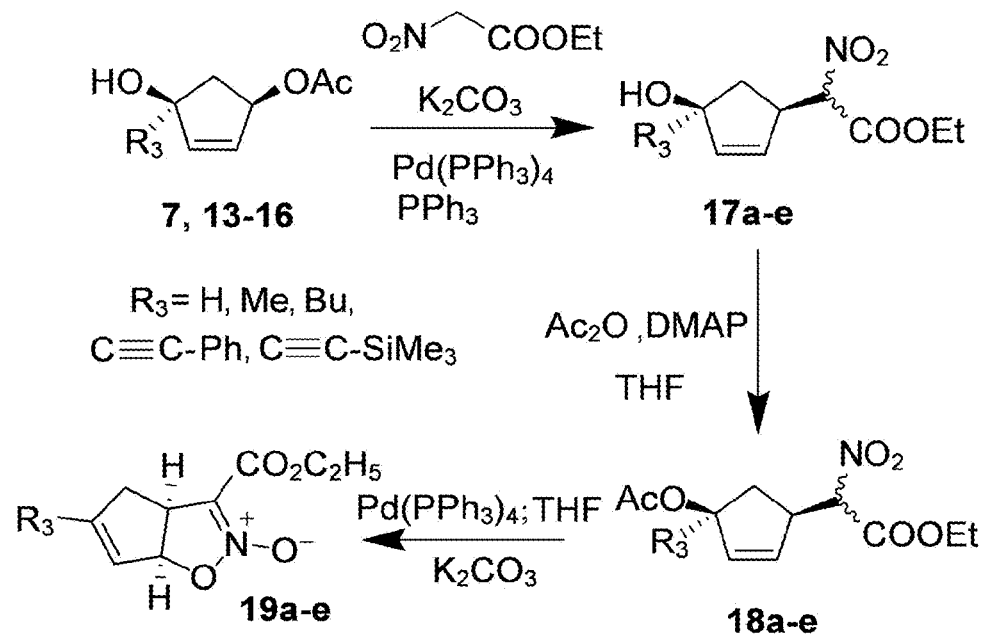
FIG. 7 is an illustration of a chemical reaction showing the synthesis of compounds 19a-e via Pd(0) catalysis.
Figure 8:
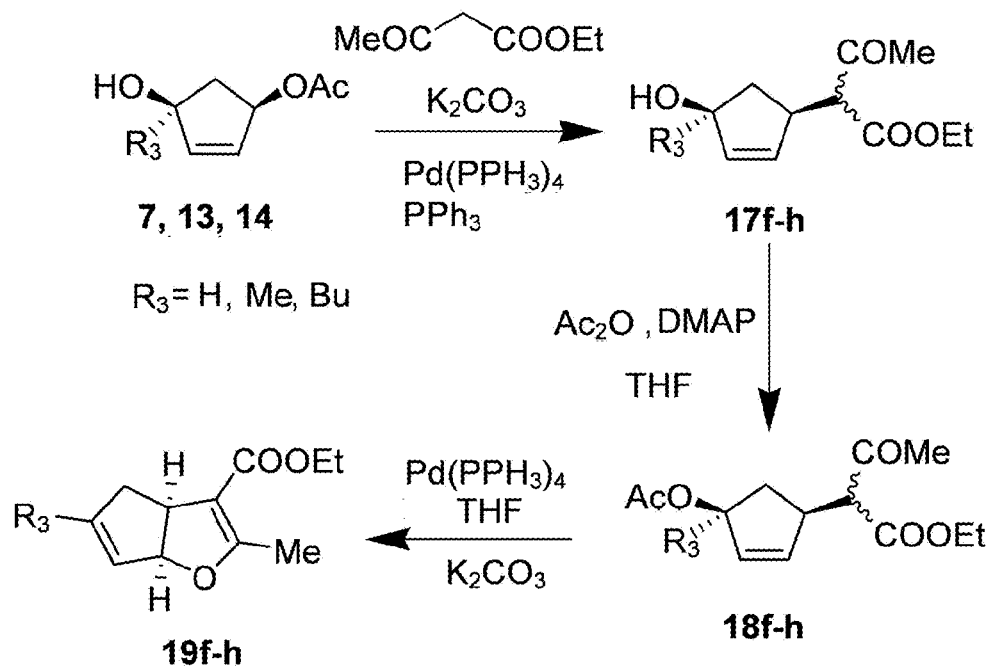
FIG. 8 is an illustration of a chemical reaction showing scheme 3, a method for synthesis of compounds 19f-h.
Figure 9:
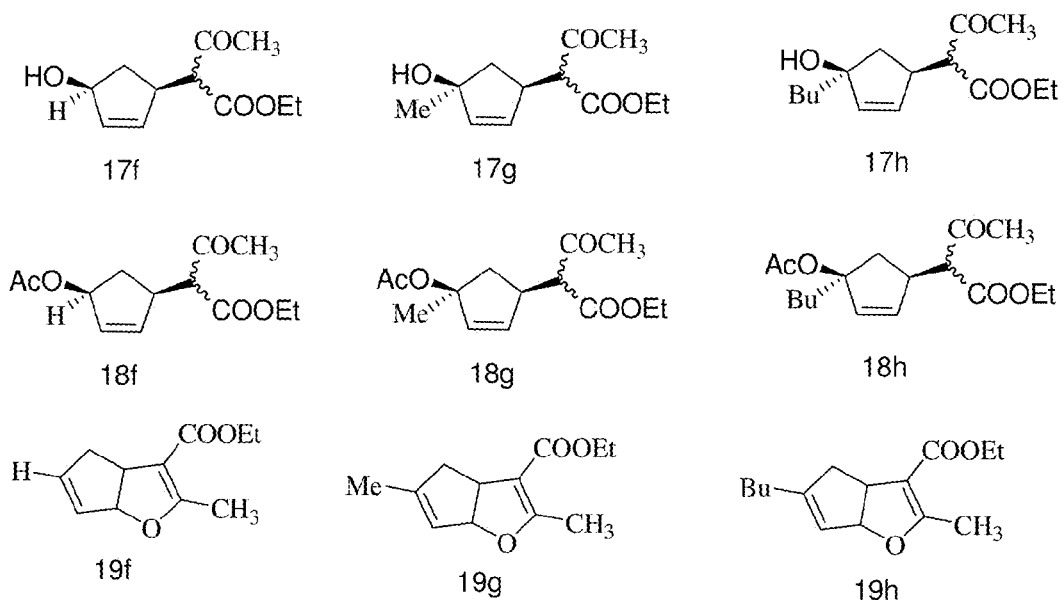
FIG. 9 depicts compounds synthesized using scheme 3, illustrated in FIG. 4.
Figure 10:
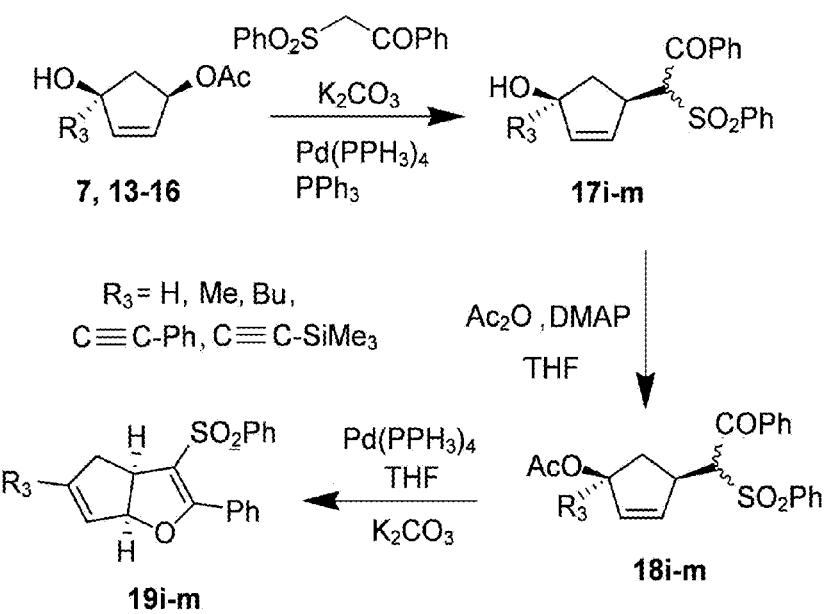
FIG. 10 is an illustration of a chemical reaction showing scheme 4, a method for synthesizing compounds19 i-m.
Figure 11:
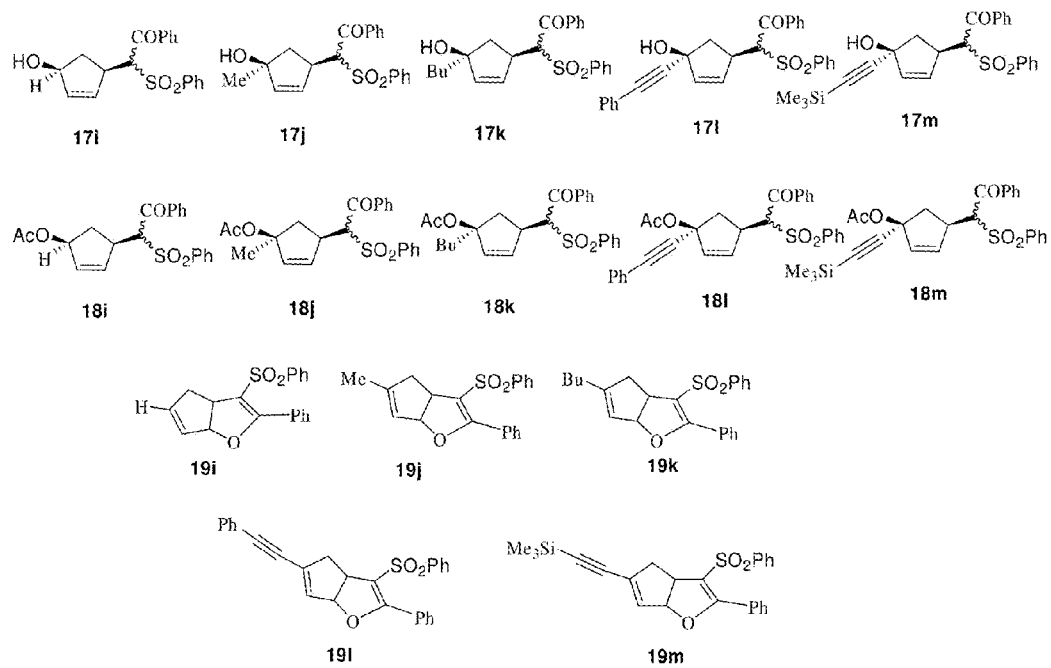
FIG. 11 depicts compounds synthesized using scheme 4, illustrated in FIGS. 1 and 4.

Isoxazoline-2-oxides 19a-e, seen in FIG. 5, were obtained in good to excellent yield and in optically pure form upon treating the acetates 18a-c, in presence of K$_2$CO$_3$ and palladium tetrakistriphenylphosphine, seen in FIGS. 6 and 7. Similar reaction with the acetates 18f-m, seen in FIGS. 8 and 10, led to the formation of the substituted dihydrofurans 19f-m, seen in FIGS. 9 and 11, in optically pure form, seen in FIG. 12.

The cyclization reactions were also evaluated in presence of various bases, i.e., NaH, K$_2$CO$_3$, and KO$^t$Bu, seen in FIG. 6, in THF using catalytic amount of Pd(0) catalysts. The yield of the reaction was independent of the base used. For all reactions recorded in FIG. 12, K$_2$CO$_3$ was used as the base. Pd(PPh$_3$)$_4$ and Pd$_2$(dba)$_3$ were the two Pd(0) catalysts evaluated in this reaction and identical results were obtained. Pd(II) catalysts like PdCl$_2$ did not catalyze the cyclization.

Figures 12, 13:
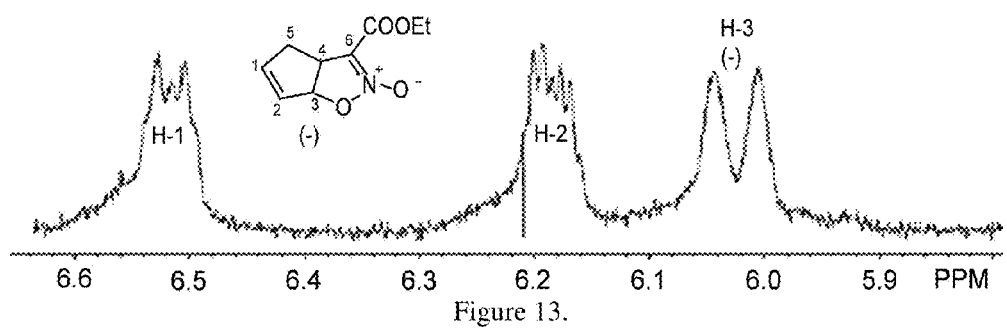
FIG. 12 is a table of compounds 19a-m, using Pd catalyzed cyclization.
FIG. 13 is a graph of $^1H$ NMR of enantioenriched compound 19a, in the presence of (+)—$Eu(hfc)_3$. The % ee was calculated using H-3 signals, where the absence of a doublet at 5.9 ppm indicates a >97% ee.

FIGS. 13 and 14 show $^1$H NMR comparison of racemic and enantioenriched 19a in presence (+)—Eu(hfc)$_3$. The H-3 signals were used for calculation of % ee. The absence of doublet at 5.9 ppm in enantioenriched 19a indicates a >97% ee. Interestingly, compound 18p led to an unusual product 19p, which most probably results from an interconversion between the two π-allyl complexes I and II.

Pd catalyzed cyclization produces optically pure furan and isoxazoline-2-oxide analogs under mild reaction conditions. The method involves tandem use of the enzymatic and chemical catalysis. The key step is the desymmetrization of the meso diacetate (6) using commercially available *P. cepacia* lipase (PS-30), in high ee. This work provides a novel pathway to obtain optically pure furan and isoxazoline-2-oxide analogs, such as those seen in FIG. 15, which are rather difficult to obtain via previous strategies.

Example 1

(+)-(1S,4R)-4-Acetoxylcylcopent-2-en-1-ol (7)
(Crandall, J. K.; et al. *J. Org. Chem.* 1968, 33, 423;
Deardorff, D. R.; Matthews, A. J.; et al. *Tetrahedron Lett.* 1986, 27, 1255).

meso-Diacetate 6 (Siddiqi, S. M.; et al. *Nucleosides Nucleotides* 1993, 12, 267), (10 g, 0.054 mol) was taken in a mixture of phosphate buffer (pH 7.0; 75 ml) and acetone (5 ml) in a round bottom flask. Lipase PS-30 (500 mg) was added while maintaining the pH of the reaction mixture at 7.0 using 1N NaOH solution. The reaction was stopped when no change in the pH of the reaction medium occurred. The conversion at this point was estimated to be ~60% by TLC. The reaction mixture was extracted with ethyl acetate (3×200 mL). The organic layer was dried over Na$_2$SO$_4$ and concentrated by rotoevaporation. The crude product was subjected to column chromatography over silica gel using ethyl acetate/hexane (1:3) to isolate the monoacetate 7 as a white solid, mp 40-42° C.; $[\alpha]^{20}_D$+68.9 (CHCl$_3$); lit (Deardorff, D. R.; et al. *Tetrahedron Lett.* 1986, 27, 1255). $[\alpha]^{20}_D$+69.6 (CHCl$_3$); $^1$H NMR (CDCl$_3$, 400 MHz): δ 1.60 (dt, 1H, J=14.8, 4.0 Hz), 2.01 (s, 3H), 2.76 (p, 1H, J=7.2 Hz), 4.6 (m, 1H), 5.4 (m, 1H), 5.94 (d, 1H, J=4.0 Hz), 6.06 (m, 1H) ppm; $^{13}$C NMR (CDCl$_3$, 100 MHz): δ 20.5, 40.4, 74.6, 77.2, 132.3, 139.1, 171.3 ppm.

Example 2

(R)-4-Acetoxy-2-cyclopenten-1-one (8) (Paquette, L. A.; et al. *Org. Synth.* 1996, 73, 36).

Viscous liquid; $^1$H NMR (CDCl$_3$, 250 MHz): δ 2.03 (s, 3H), 2.22 (dt, 1H, J=18.7, 2.2 Hz), 2.73 (dt, 1H, J=19.0, 6.75 Hz), 5.78 (m, 1H), 6.26 (d, 1H, J=5.7 Hz), 7.5 (m, 1H) ppm; $^{13}$C NMR (CDCl$_3$, 62.5 MHz): δ 20.8, 40.9, 71.9, 136.9, 158.9, 170.4, 204.8 ppm.

Example 3

General Procedure for Preparation of Compounds 9-12.

To a solution of (R)-4-acetoxy-2-cyclopenten-1-one 8 (200 mg, 1.428 mmol) in freshly distilled ether (15 ml) at −78° C. was added 1.6 M solution of methyl lithium in ether (3.57 ml, 5.712 mmol) under a nitrogen atmosphere. The reaction was allowed to stir for 1 h and was quenched using NH$_4$Cl solution. The product was purified by column chromatography using ethyl acetate/hexane (2:1) to afford 9 (150 mg, yield=92%) as a viscous liquid.

(1S,4R)-1-Methylcyclopent-2-ene-1,4-diol (9).

Viscous liquid; $[\alpha]^{20}_D$+55.2 (c 0.02, acetone); $^1$H NMR (CDCl$_3$, 250 MHz): δ 1.27 (s, 3H, CH$_3$), 1.71 (dd, 1H, J=14.5, 2.7 Hz), 2.29 (dd, 1H, J=14.5, 7.2 Hz), 3.9 (br s, 2H), 4.58 (d, 1H, J=6.2 Hz), 5.79 (m, 2H) ppm; $^{13}$C NMR (CDCl$_3$, 62.5 MHz): δ 27.5, 49.5, 75.2, 81.2, 134.0, 141.0 ppm. HRESIMS calculated for C$_6$H$_{11}$O$_2$ ([M+H]$^+$): 115.0759; found: 115.0758.

(1S,4R)-1-Butyl-cyclopent-2-ene-1,4-diol (10).

Viscous liquid; $[\alpha]^{20}_D$+50.2 (c 0.03, CH$_2$Cl$_2$); $^1$H NMR (CDCl$_3$, 250 MHz): δ 0.81 (t, 3H, CH$_3$, J=6.7 Hz), 1.24 (m, 2H), 1.55 (m, 5H, H-4+OH), 1.60 (dd, 1H, J=5.5, 3.2 Hz), 2.03 (s, 1H, OH), 2.31 (dd, 1H, J=14.2, 7.0 Hz), 4.60 (d, 1H, J=5.5 Hz), 5.83 (m, 2H) ppm; $^{13}$C NMR (CDCl$_3$, 62.5 MHz): δ 14.0, 23.0, 26.5, 40.1, 48.2, 75.4, 84.1, 135.0, 140.0 ppm. HRESIMS calcd for C$_9$H$_{17}$O$_2$ ([M+H]$^+$): 157.1229; found: 157.1221.

(1S,4R)-1-Phenylethynyl-cyclopent-4-ene-1,4-diol (11).

White solid: mp=114-116° C.; $[\alpha]^{20}_D$+330.5 (c 0.11, acetone); $^1$H NMR (CDCl$_3$, 250 MHz): δ 1.97 (s, 1H, OH), 2.00 (s, 1H, OH), 2.04 (dd, 1H, J=14.0, 3.2 Hz), 2.82 (dd, 1H, J=14.0, 6.7 Hz), 4.78 (dd, 1H, J=6.7, 3.2 Hz), 6.01 (s, 2H), 7.26-7.32 (m, 5H) ppm; $^{13}$C NMR ((CD$_3$)$_2$CO, 62.5 MHz): δ 52.4, 75.0, 76.2, 83.3, 93.3, 123.9, 129.1, 129.3, 132.2, 136.9, 137.7 ppm. HRESIMS calcd for C$_{13}$H$_{13}$O$_2$ ([M+H]$^+$): 201.0916; found: 201.0921.

X-ray crystallographic data for (11).

In the crystal of (1S,4R)-1-phenylethynyl-cyclopent-4-ene-1,4-diol, four molecules were found in each unit cell. The compound crystallized in an orthorhombic space group P2(1), with cell dimensions a=5.3082(10) Å, b=8.4869(16) Å, c=17.005(3) Å. A total of 5642 unique reflection data were obtained to give a final R index [I>2σ(I)] of R1=0.0337, wR2=0.0894 and R indices (all data) R1=0.0365, wR2=0.0918.

TABLE 1

| Identification code | kb0725 |
|---|---|
| Empirical formula | C$_{13}$H$_{12}$O$_2$ |
| Formula weight | 200.23 |
| Temperature | 100(2) K |
| Wavelength | 0.71073 Å |
| Crystal system | Orthorhombic |
| Space group | P2(1)2(1)2(1) |
| Unit cell dimensions | a = 6.2734(9) Å ☐ = 90°. |
| | b = 7.6864(11) Å ☐ = 90°. |
| | c = 22.307(3) Å ☐ = 90°. |
| Volume | 1075.6(3) Å$^3$ |
| Z | 4 |
| Density (calculated) | 1.236 Mg/m$^3$ |
| Absorption coefficient | 0.083 mm$^{-1}$ |
| F(000) | 424 |
| Crystal size | 0.30 × 0.20 × 0.12 mm$^3$ |
| Theta range for data collection | 1.83 to 25.10°. |
| Index ranges | −7 <= h <= 7, −9 <= k <= 7, −26 <= l <= 22 |
| Reflections collected | 5642 |
| Independent reflections | 1900 [R(int) = 0.0306] |
| Completeness to theta = 25.10° | 99.7% |
| Absorption correction | SADABS |
| Max. and min. transmission | 1.000 and 0.761 |
| Refinement method | Full-matrix least-squares on F$^2$ |
| Data/restraints/parameters | 1900/0/141 |
| Goodness-of-fit on F$^2$ | 0.872 |
| Final R indices [I > 2sigma(I)] | R1 = 0.0337, wR2 = 0.0894 |
| R indices (all data) | R1 = 0.0365, wR2 = 0.0918 |

(1S,4R)-1-Trimethylsilanylethynyl-cyclopent-4-ene-1,4-diol (12).

Viscous liquid; $[\alpha]^{20}_D$+278.2 (c 0.03, CH$_2$Cl$_2$); $^1$H NMR (CDCl$_3$, 250 MHz): δ 0.23 (s, 9H), 1.90 (br s, 1H, OH), 1.94 (dd, 1H, J=14.2, 3.5 Hz), 2.47 (s, 114, OH), 2.72 (dd, 1H, J=14.2, 7.0 Hz), 4.72 (m, 1H), 5.91 (d, 1H, J=5.5 Hz), 5.97 (dd, 1H, J=5.5, 2.0 Hz) ppm; $^{13}$C NMR (CDCl$_3$, 62.5 MHz): δ-0.5, 50.6, 75.0, 75.6, 85.3, 105.8, 136.5, 137.4 ppm. HRESIMS calcd for C$_{10}$H$_{17}$O$_2$Si ([M+H]$^+$): 197.0998; found: 197.0995.

Example 4

General Procedure for Preparation of Compounds (13-16).

To a solution of 9 (100 mg, 0.877 mmol) in dry THF (10 ml) at room temperature was added acetic anhydride (89 mg, 0.877 mmol), and catalytic amount of DMAP. The reaction was allowed to stir for 3 h and then concentrated. The residue was taken in ethyl acetate (40 ml) and was treated twice with saturated sodium bicarbonate solution (20 ml), followed by brine (10 ml). The organic layer was dried over sodium sulfate and the resulting product 13 was purified by column chromatography using ethyl acetate/hexane (1:2) (80.25 mg, yield=58.77%).

(1R,4S)-4-Hydroxy-4-methyl-2-cyclopenten-1-yl acetate (13).

$^1$H NMR (CDCl$_3$, 250 MHz): δ 1.32 (s, 3H), 1.80 (dd, 1H, J=14.5, 3.5 Hz), 1.97 (s, 314, 1H), 2.2 (br s, 1H), 2.36 (dd, 1H, J=14.5, 7.5 Hz), 5.46 (m, 114), 5.76 (d, 1H, J=5.5 Hz), 5.92 (d, 1H, J=5.5 Hz) ppm; $^{13}$C NMR (CDCl$_3$, 62.5 MHz): δ 21.2, 27.3, 46.7, 77.6, 80.9, 130.2, 143.2, 170.8 ppm. HRESIMS calcd for C$_8$H$_{13}$O$_3$ ([M+H]$^+$): 157.0865; found: 157.0871.

(1R,4S)-4-Hydroxy-4-butyl-2-cyclopenten-1-yl acetate (14).

Viscous liquid; $^1$H NMR (CDCl$_3$, 250 MHz): δ 0.84 (t, 3H, J=6.7 Hz), 1.26 (m, 4H), 1.54 (m, 2H), 1.72 (m, 2H, 1H+OH) 1.97 (s, 3H), 2.40 (dd, 114, J=14.7, 7.5 Hz), 5.43 (m, 114), 5.80 (dd, 114, J=5.5, 2.2 Hz), 5.91 (dd, 1H, J=4.7, 0.7 Hz); $^{13}$C NMR (CDCl$_3$, 62.5 MHz): δ 14.0, 21.2, 23.1, 26.4, 40.0, 45.0, 77.5, 83.8, 131.0, 142.0, 170.9 ppm. HRESIMS calcd for C$_{11}$H$_{19}$O$_3$ ([M+H]$^+$): 199.1334; found: 199.1333.

(1R,4S)-4-Hydroxy-4-phenylethynyl-2-cyclo-penten-1-yl acetate (15).

Viscous liquid; $^1$H NMR (CDCl$_3$, 250 MHz): δ 1.98 (s, 3H), 2.09 (dd, 1H, J=14.5, 3.7 Hz), 2.82 (s, 1H), 2.91 (dd, 1H, J=14.5, 7.2 Hz), 5.6 (m, 1H), 5.92 (dd, 114, J=5.5, 2.2 Hz), 6.07 (d, 114, J=5.5 Hz), 7.20-7.35 (m, 5H) ppm; $^{13}$C NMR (CDCl$_3$, 62.5 MHz): δ 21.2, 47.8, 76.0, 77.1, 84.5, 90.2, 122.2, 128.3, 128.6, 131.6, 132.0, 139.7, 170.9 ppm. HRESIMS calcd for C$_{15}$H$_{15}$O$_3$ ([M+H]$^+$): 243.1021; found: 243.1018.

(1R,4S)-4-Hydroxy-4-trimethylsilanylethynyl-2-cyclopenten-1-yl acetate (16).

$^1$H NMR (CDCl$_3$, 250 MHz): δ 0.20 (s, 9H), 1.99 (s, 3H), 2.02 (dd, 1H, J=14.5, 3.7 Hz), 2.50 (s, 114, OH), 2.84 (dd, 1H, J=14.5, 7.5 Hz), 5.54 (m, 1H), 5.93 (dd, 1H, J=5.2, 2.0 Hz), 6.00 (d, 1H, J=5.5 Hz) ppm; $^{13}$C NMR (CDCl$_3$, 62.5 MHz): δ −0.3, 21.1, 47.5, 75.4, 76.8, 85.0, 105.9, 132.6, 139.9, 170.7 ppm. HRESIMS calcd for C$_{12}$H$_{19}$O$_3$Si ([M+Hi]$^+$): 239.1104; found: 239.1101.

Example 5

General Procedure for Preparation of Compounds 17a-p.

To a solution of ethyl nitroacetate (100 mg, 0.752 mmol) in dry THF (10 ml) at room temperature was added potassium carbonate (110 mg, 0.800 mmol) under a nitrogen atmosphere. The reaction was allowed to stir for 20 min and Pd(PPh$_3$)$_4$ (43.4 mg, 0.037 mmol), PPh$_3$ (197 mg, 0.752 mxnol), and monoacetate 7 (106 mg, 0.752 mmol) dissolved in 5 ml THF was added to it. The reaction was allowed to stir at 40° C. for 12 h and then vacuum filtered through Celite with subsequent concentration of the filtrate. The product was purified by column chromatography using ethyl acetate/hexane (1:2) to afford 17a (120 mg, yield=62%) as a yellow viscous liquid.

Example 6

Ethyl (2R/S,1'R,4'S)-2-(4'-hydroxy-2'-cyclopenten-1'-yl)-2-nitroacetate (17a).

Viscous yellow liquid; $^1$H NMR (CDCl$_3$, 400 MHz): δ 1.25 (t, 3H, J=7.2 Hz), 1.57 (m, 1H), 1.92 (br s, 1H), 2.50 (m, 1H), 3.46 (t, 1H, J=2.4 Hz), 4.23 (q, 214, J=6.8 Hz), 4.79 (br 5, 1H), 5.06 (t, 1H, J=8.0 Hz), 5.74-5.83 (dd, 1H, J=6.0, 4.8 Hz), 5.95-5.97 (m, 1H); $^{13}$C NMR (CDCl$_3$, 100 MHz): δ 14.0, 36.2, 36.8, 45.4, 45.1, 63.3, 76.0, 76.3, 91.0, 91.4, 131.6, 132.0, 137.7, 137.9, 163.8, 163.9 ppm. HRESIMS calcd for C$_9$H$_{14}$NO$_5$ ([M+H]$^+$): 216.0872; found: 216.0875.

Example 7

Ethyl (2R/S,1'R,4'S)-2-(4'-hydroxy-4-methyl-2'-cyclopenten-1'-yl)-2-nitroacetate (17b).

Viscous yellow liquid; $^1$H NMR (CDCl$_3$, 250 MHz): δ 1.21 (t, 3H, J=7.5 Hz), 1.34 (s, 3H), 1.79 (dt, 1H, J=14.2, 5.0 Hz), 1.95 (br s, 1H), 2.19 (dd, 1H, J=14.2, 8.2 Hz), 3.50 (m, 1H), 4.19 (q, 2H, J=7.5 Hz), 5.03 (t, 1H, J=8.2 Hz), 5.59 (2dd, 1H, J=5.5, 2.0 Hz), 5.82 (dt, 1H, J=5.5, 2.0 Hz) ppm; $^{13}$C NMR (CDCl$_3$, 62.5 MHz): δ 13.9, 27.5, 27.6, 42.2, 42.8, 45.1, 45.5, 63.1, 82.1, 82.4, 90.6, 91.0, 129.1, 129.6, 141.8, 142.1, 163.7 ppm. HRESIMS calcd for C$_{10}$H$_{16}$NO$_5$ ([M+H]$^+$): 230.1029; found: 230.1034.

Example 8

Ethyl (2R/S,1'R,4'S)-2-(4'-hydroxy-4-butyl-2'-cyclopenten-1'-yl)-2-mtroacetate (17c).

Viscous yellow liquid; $^1$H NMR (CDCl$_3$, 250 MHz): δ 0.90 (t, 314, J=7.0 Hz), 1.2-1.4 (m, 7H, 2CH$_2$+CH$_3$), 1.61 (t, 2H, J=7.0 Hz), 1.75 (dt, 1H, J=14.2, 4.5 Hz), 1.89 (s, OH), 2.30 (dd, 1H, J=14.2, 8.2 Hz), 3.53 (m, 1H), 4.26 (q, 2H, J=7.2 Hz), 5.15 (dd, 1H, J=8.2, 6.5 Hz), 5.70 (dd, 0.5H, J=5.7, 2.0 Hz), 5.77 (dd, 0.5H, J=5.7, 2.2 Hz), 5.88 (dt, 1H, J=5.5, 2.2 Hz) ppm; $^{13}$C NMR (CDCl3, 62.5 MHz): δ 13.9, 14.0, 23.0, 26.3, 40.4, 41.0, 45.2, 45.4, 63.1, 85.1, 91.1, 129.8, 130.2, 140.7, 140.9, 161.5 ppm. HRESIMS calcd for C$_{13}$H$_{22}$NO$_5$ ([M+H]$^+$): 272.1498; found: 272.1493.

Example 9

Ethyl (2R/S,1'R,4'S)-2-(4'-hydroxy-4-phenyl-ethynyl-2'-cyclopenten-1'-yl)-2 nitroacetate (17d).

Viscous yellow liquid; $^1$H NMR (CDCl$_3$, 250 MHz): δ 1.24 (dt, 3H, J=6.7, 1.0 Hz), 2.1 (m, 1H), 2.53 (d, 1H, J=2.7 Hz, OH), 2.74 (m, 1H), 3.65 (m, 1H), 4.19 (q, 2H, J=6.7 Hz), 5.06 (dd, IH, J=9.0, 1.0 Hz), 5.79, 5.87 (2dd, 1H, J=5.5, 2.0 Hz), 6.00 (dt, 1H, J=5.5, 1.7 Hz), 7.22-7.36 (m, 5H) ppm; $^{13}$C NMR (CDCl$_3$, 62.5 MHz): δ 13.9, 43.7, 44.4, 44.9, 45.2, 63.21, 63.26, 76.5, 77.5, 85.2, 89.8, 90.6, 90.8, 122.1, 128.3, 128.7, 131.5, 131.6, 132.0, 138.8, 138.9, 163.5 ppm. HRESIMS calcd for C$_{17}$H$_{18}$NO$_5$ ([M+H]$^+$): 316.1185; found: 316.1180.

Example 10

Ethyl (2R/S,1'R,4'S)-2-(4'-hydroxy-4-trimethylsila-nylethynyl-2'-cyclopenten-1'-yl)-2-nitroacetate (17e).

Viscous yellow liquid, $^1$H NMR (CDCl$_3$, 250 MHz): 00.19 (s, 9H), 1.21 (t, 3H, J=7.0 Hz, CH3), 1.93 (m, 1H), 2.50 (s, 1H, OH), 2.74 (m, 1H), 3.62 (m, 1H), 4.20 (q, 2H, J=6.7 Hz, CH$_2$), 5.03 (dd, 1H, J=9.0, 1.0 Hz), 5.75-5.81 (2dd, 1H, J=5.5, 2.0 Hz), 6.01 (dt, 1H, J=5.5, 1.7 Hz) ppm; $^{13}$C NMR (CDCl$_3$, 62.5 MHz): 6-0.2, 14.0, 42.7, 44.2, 60.5, 72.3, 75.4, 85.2, 90.8, 132.6, 148.1, 167.3 ppm. HRESIMS calcd for C$_{14}$H$_{22}$NO$_5$Si ([M+H]$^+$): 312.1267; found: 312.1264.

Example 11

Ethyl (2R/S,1'R,4'S)-2-(4'-hydroxy-2'-cyclopenten-1'-yl)-3-oxobutanoate (17f).

Viscous yellow liquid; $^1$H NMR (CDCl$_3$, 250MHz): δ 1.18 (t, 3H, J=7.2Hz), 1.28 (t, IH, J=7.0 Hz), 2.18 (s, 3H), 2.37 (p, 1H, J=7.2 Hz), 3.19 (m, 1H), 3.45 (m, 1H), 4.14 (q, 2H, J=7.2 Hz), 4.6 (m, 1H), 5.67-5.83 (m, 2H) ppm; $^{13}$C NMR (CDCl$_3$, 62.5 MHz): δ 14.2, 29.7, 29.9, 37.2, 37.8, 43.1, 43.2, 61.0, 64.7, 65.1, 76.22, 76.28, 134.2, 134.6, 135.2, 135.5, 168.7, 169.0, 202.61, 202.66 ppm. HRESIMS calcd for C$_{11}$H$_{17}$O$_4$ ([M+H]$^+$): 213.1127; found: 213.1134.

Example 12

Ethyl (2R/S,1'R,4'S)-2-(4'-hydroxy-4-methyl-2'-cyclopenten-1'-yl)-3-oxobutanoate (17g).

Viscous yellow liquid; $^1$H NMR (CDCl$_3$, 250 MHz): δ 1.20 (t, 3H, J=7.0 Hz), 1.29 (s, 3H), 1.50-1.71 (2dd, 1H, J=14.0, 5.2 Hz), 2.16 (m, CH$_3$+H-5), 2.55 (br s, 1H, OH), 3.24 (m, 1H), 3.47 (dd, 1H, J=8.7, 3.0 Hz), 4.13 (q, 2H, J=7.0 Hz), 5.52-5.62 (2dd, 1H, J=5.2, 2.5 Hz), 5.7 (dd, 1H, J=5.5, 2.0 Hz) ppm; $^{13}$C NMR (COG3, 62.5 MHz): δ 14.0, 27.5, 29.6, 30.0, 43.3, 43.5, 43.6, 44.2, 61.4, 64.1, 64.2, 82:2, 82.3, 131.8, 132.3, 139.7, 140.0, 168.8, 169.1, 202.3 ppm. HRESIMS calcd for C$_{12}$H$_{19}$O$_4$ ([M+H]$^+$): 227.1283; found: 227.1280.

Example 13

Ethyl (2RIS,i'R,4'S)-2-(4'-hydroxy-4-butyl-2'-cyclopenten-1'-yl)-3-oxobutanoate (17h).

$^1$H NMR (CDCl$_3$, 250 MHz): 00.83 (t, 3H, J=7.0 Hz), 1.21 (m, 7H, CH$_3$+2CH$_2$), 1.50 (m, 4H, 1H+CH$_2$+OH), 2.17 (m, 4H, CH$_3$+1H), 3.21 (m, 1H), 3.45 (dd, 1H, J=5.2, 3.0 Hz), 4.11 (q, 2H, J=7.0 Hz), 5.67 (m, 2H) ppm; $^{13}$C NMR (CDCl$_3$, 62.5 MHz): δ 13.0, 13.1, 22.1, 25.4, 25.6, 28.6, 29.0, 39.45, 39.47, 41.2, 41.4, 42.3, 42.5, 60.5, 63.3, 63.4, 84.1, 84.4, 132.1, 133.4, 137.1, 137.4, 167.8, 201.4 ppm. HRESIMS calcd for C$_{15}$H$_{25}$O$_4$ ([M+H]$^+$): 269.1753; found: 269.1756.

Example 14

2-Phenylsulfonyl (2R/S,1'R,4'S)-2-(4'-hydroxy-2'-cyclopenten-1'-yl)-1-phenyl-ethanone (17i).

Viscous yellow liquid; $^1$H NMR (CDCl$_3$, 250 MHz): δ 1.26-2.2 (dt, 1H, J=14.0, 4.5 Hz), 2.52 (m, 2H), 3.32 (m, 1H), 4.67-4.80 (m, 1H), 5.05 (dd, 1H, J=21.2, 9.5 Hz), 5.45-5.49 (ddd, 1H, J=5.7, 2.5, 1.0 Hz), 5.8-5.9 (dt, 1H, J=5.7, 2.5 Hz), 7.3-7.7(m, 10H) ppm; $^{13}$C NMR (CDCl$_3$, 62.5 MHz): δ 38.2, 38.4, 43.5, 44.0, 74.0, 74.3, 75.7, 128.7, 128.8, 128.9, 129.7, 129.8, 133.7, 134.0, 134.2, 134.6, 136.2, 137.1, 137.17, 192.9, 193.3 ppm. HRESIMS calcd for C$_{19}$H$_{19}$O$_4$S ([M+H]$^+$): 343.1094; found: 343.1097.

Example 15

2-Phenylsulfonyl (2R/S,1'R,4'S)-2-(4'-hydroxy-4-methyl-2'cyclopenten-1'-yl)-1-phenyl-ethanone (17j).

Viscous yellow liquid; $^1$H NMR (CDCl$_3$, 250 MHz): δ 1.36 (s, 3H), 1.49 (dd, 1H, J=14.0, 5.0 Hz), 2.05 (m, 1H), 2.29 (s, 1H, OH), 3.16-3.39 (m, 1H), 5.14 (dd, 1H, J=9.7, 2.5 Hz), 5.53, 5.78 (from 2 diastereomers) (2dd, 1H, J=5.5, 2.5 Hz), 6.14 (dd, 1H, J=5.2, 1.7 Hz), 7.29-7.86 (m, IOH); $^{13}$C NMR (CDCl$_3$, 62.5 MHz): δ 27.5, 29.6, 43.3, 43.5, 43.6, 44.2, 64.1, 64.2, 82.2, 82.3, 127.9, 128.4, 128.5, 128.74, 128.76, 130.1, 130.4, 131.8, 132.3, 132.6, 133.8, 180.9, 190.4 ppm. HRESIMS calcd for C$_{20}$H$_{21}$O$_4$S ([M+H]$^+$): 357.1161; found: 357.1158.

Example 16

2-Phenylsulfonyl (2R/S,1'R,4'S)-2-(4'-hydroxy-4-butyl-2'-cyclopenten-1'-yl)-1-phenyl-ethanone (17k).

Viscous yellow liquid; $^1$H NMR (CDCl$_3$, 250 MHz): δ 0.79 (t, 3H), 1.18 (m, 4H, 2CH$_2$), 1.46 (m, 3H, CH2+1H), 1.89 (s, 1H, OH), 2.01 (dd, 1H, J=13.7, 8.0 Hz), 3.40 (m, 1H), 5.15 (d, 1H, J=9.7 Hz), 5.35 (dd, 0.5H, J=5.5, 1.7 Hz), 5.68 (dd, 0.5H, J=5.5, 2.0 Hz), 5.78 (dd, 0.5H, J=5.5, 1.5 Hz), 6.23 (dd, 0.5H, J=5.7, 2.0 Hz), 7.29-7.86 (m, 1OH, COPh+PhSO$_2$) ppm; $^{13}$C NMR (CDCl$_3$, 62.5 MHz): δ 12.8, 22.0, 25.3, 25.4, 39.3, 39.5, 41.5, 41.6, 42.6, 43.2, 72.9, 73.0, 83.4, 84.4, 127.73, 127.79, 127.8, 128.6, 128.7, 131.1, 132.0, 132.9, 133.1, 136.0, 136.2, 138.2, 191.9 ppm. HRESIMS calcd for C$_{23}$H$_{27}$O$_4$S ([M+H]$^+$): 399.1630; found: 399.1634.

Example 17

2-Phenylsulfonyl (2R/S,1'R,4'S)-2-(4'-hydroxy-4-phenyl-ethynyl-2'-cyclopenten-1'-yl)-1-phenyl-ethanone (17I).

Viscous yellow liquid; $^1$H NMR (CDCl$_3$, 250 MHz): δ 1.72 (dd, 0.5H, J=14.2, 4.0 Hz), 2.47 (dd, 0.5H, J=14.2, 7.2 Hz), 2.73 (m, 2H), 3.47 (m, 1H), 5.15 (dd, 0.5H, J=15.0, 10.0 Hz), 5.49 (dd, 0.5H, J=5.2, 2.0 Hz), 5.84 (dd, 1H, J=5.2, 1.5 Hz), 5.99 (dd, 0.5H, J=5.2, 1.0 Hz), 6.47 (dd, 0.5H, J=5.2, 2.2 Hz), 7.15-7.86 (m, 15H) ppm; $^{13}$C NMR (dOd3, 62.5 MHz): δ 43.5, 44.1, 45.4, 45.7, 73.5, 73.9, 76.5, 77.4, 84.9, 85.0, 90.2, 90.4, 122.2, 122.3, 128.3, 128.3, 128.5, 128.8, 128.92, 128.97, 129.7, 129.8, 131.6, 131.7, 133.9, 134.1, 134.2, 135.1, 136.9, 137.04, 137.08, 137.2, 137.6, 192.8, 193.2 ppm. HRESIMS calcd for C$_{27}$H$_{23}$O$_4$S ([M+H]$^+$):443.1317; found: 443.1321.

Example 18

Ethyl (2R/S,1'R,4'S)-2-(4'-hydroxy-4-trimethyl-silanylethynyl-2'-cyclopenten-1'-yl)-1-phenyl-ethanone (17m).

Viscous yellow liquid; $^1$H NMR (CDCl$_3$, 250 MHz): δ 0.19 (s, 9H), 1.85 (dd, 1H, J=14.2, 4.0 Hz), 2.47 (s, 1H, OH), 2.73 (m, 1H), 3.49 (m, 1H), 5.14 (d, 1H, J=10.0 Hz), 5.45 (dd, 0.5H, J=5.2, 2.0 Hz), 5.79 (dd, 0.5H, J=5.2, 1.5 Hz), 5.97 (dd, 0.5H, J=5.2, 1.0 Hz), 6.37 (dd, 0.5H, J=5.2, 2.2 Hz), 7.15-7.86 (m, 10H) ppm; $^{13}$C NMR (CDCl$_3$, 62.5 MHz): δ-0.3, 43.52, 43.56, 45.4, 45.5, 73.71, 73.74, 75.23, 75.29, 87.9, 89.0, 106.1, 106.2, 122.3, 123.0, 128.4, 128.5, 129.01, 129.08, 130.4, 133.9, 135.1, 136.1, 137.8, 140.5, 140.6, 197.5, 197.6 ppm. HRESIMS calcd for C$_{24}$H$_{27}$O$_4$SSi ([M+H]$^+$): 439.1399; found: 439.1395.

Example 19

Ethyl (2R/S,1'R,4'S)-2-(4'-hydroxy-2'-cyclo-penten-1'-yl)-2 cyanoacetate (17n).

Viscous yellow liquid; $^1$H NMR (CDCl$_3$, 250 MHz): δ 1.27 (t, 3H, J=7.7 Hz), 1.5 (tt, 1H, J=14.2, 4.0 Hz), 2.47 (s, 1H, OH), 2.56 (m, 1H), 3.23 (m, 1H), 3.53 (d, 1H, J=6.7 Hz), 4.2 (q, 2H, J=7.7 Hz), 4.76 (m, 1H), 5.73-5.83 (dt, 1H, J=5.5, 1.2 Hz), 5.99 (m, 1H) ppm; $^{13}$C NMR (CDCl$_3$, 62.5 MHz): δ 13.9, 36.8, 43.0, 44.5, 44.8, 62.9, 76.0, 76.1, 116.1, 116.2, 132.0, 132.4, 137.6, 137.7, 165.3, 165.4 ppm. HRESIMS calcd for C$_{10}$H$_{14}$NO$_3$([M+H]$^+$): 196.0974; found: 196.0977.

Example 20

Phenylsulfonyl (2R/S,1'R,4'S)-2-(4'-hydroxy-2'-cyclopenten-1'-yl)-2-acetonitrile (17o).

Viscous yellow liquid; $^1$H NMR (CDCl$_3$, 250MHz): δ 1.6 (dq, 1H, J=14.0, 4.5 Hz), 2.2 (br s, 1H, OH), 2.58 (m, 1H), 3.43 (m, 1H), 3.99 (dd, 1H, J=27.2, 4.5 Hz), 4.76 (s, 1H), 5.76-6.02 (m, 2H), 7.55-7.71 (m, 5H) ppm; $^{13}$C NMR (CDCl$_3$, 62.5 MHz): δ 37.1, 38.8, 41.6, 42.2, 61.9, 62.1, 75.8, 76.2, 113.5, 113.7, 129.4, 129.8, 131.71, 131.75, 135.43, 135.47, 136.2, 136.3, 138.32, 138.35 ppm. HRESIMS calcd for C$_{13}$H$_{14}$NO$_3$S ([M+H]$^+$): 264.0694; found: 264.0688.

Example 21

2-(4-Hydroxy-cyclopent-2-enyl)-malonic acid di-methyl ester (17p).

Viscous liquid; $^1$H NMR (CDCl$_3$, 400 MHz): δ 1.33 (m, 1H, J=14.0, 4.5 Hz), 2.35 (p, 1H, J=7.6 Hz), 3.05 (m, 2H), 3.30 (t, 1H, J=7.6 Hz), 3.58 (s, 6H), 4.63 (s, 1H), 5.67 (d, 1H, J=5.2 Hz), 5.74 (s, IH) ppm; $^{13}$C NMR (CDCl$_3$, 100 MHz): δ 37.6, 43.8, 52.6, 56.4, 76.3, 134.1, 135.9, 169.0, 169.2 ppm. HRESIMS calcd for C$_{10}$H$_{15}$O$_5$ ([M+H]$^+$): 215.0919; found: 215.0922.

Example 22

General Procedure for Preparation of Compounds (18a-p).

To a solution of 17a (100 mg, 0.465 mmol) in dry THF (10 ml) at room temperature was added acetic anhydride (51 mg, 0.5 mmol) and catalytic amount of DMAP. The reaction was allowed to stir for 3 h and then concentrated. The residue was taken up in ethyl acetate (40 ml) and extracted twice with saturated sodium bicarbonate solution (20 ml), followed by brine (10 ml). The organic layer was dried over sodium sulfate and the resulting product 18a (110 mg, yield=92%) was obtained as light yellow liquid.

Example 22

Ethyl (2R/S,1'R,4'S)-2-(4'-acetoxy-2'-cyclopenten-1'-yl)-2-nitroacetate (18a).

Viscous liquid; $^1$H NMR (CDCl$_3$, 400 MHz): δ 1.25 (t, 3H, J=7.2 Hz), 1.54 1.69 (m, 1H), 1.97 (s, 3H), 2.53-2.61 (m, 1H), 3.51 (br s, 1H), 4.25 (q, 2H, J=7.2 Hz), 4.96 (t, 1H, J=8.8 Hz), 5.58 (br s, 1H), 5.89-5.98 (m, 2H) ppm; $^{13}$C NMR (CDCl$_3$, 100 MHz): δ 14.0, 21.3, 33.2, 33.7, 44.7, 44.8, 63.3, 78.1, 78.4, 91.1, 91.3, 133.8, 134.0, 134.3, 134.7, 163.5, 170.8 ppm. HRESIMS calcd for C$_{11}$H$_{16}$NO$_6$ ([M+H]$^+$): 258.0977; found: 258.0978.

Example 24

Ethyl (2R/S,i'R,4'S)-2-(4'-acetoxy-4-methyl-2'-cyclopenten-1'-yl)-2-nitroacetate (18b).

Viscous liquid; $^1$H NMR (CDCl$_3$, 250 MHz): δ 1.21 (t, 3H, J=7.0 Hz), 1.5 (s, 3H), 1.91 (s, 3H), 2.02 (dt, 1H, J=14.2, 4.5 Hz), 2.21 (m, 1H), 3.52 (m, 1H), 4.2 (q, 2H, J=7.0 Hz), 4.99 (dd, 1H, J=9.2, 2.0 Hz), 5.71 (dd, 0.5H, J=5.5, 2.5 Hz), 5.76 (dd, 0.5H, J=5.7, 2.5 Hz), 6.13 (dt, 1H, J=5.5, 2.0 Hz) ppm; $^{13}$C NMR (CDCl$_3$, 62.5 MHz): δ 13.9, 22.0, 24.5, 24.6, 40.3, 41.0, 44.5, 45.0, 63.1, 90.1, 90.4, 90.8, 131.2, 131.6, 138.6, 138.8, 163.5, 170.4 ppm. HRESIMS calcd for C$_{12}$H$_{18}$NO$_6$ ([M+H]$^+$): 272.1134; found: 272.1131.

Example 25

Ethyl (2R/S,1'R,4'S)-2-(4'-acetoxy-4-phenyl-ethynyl-2'-cyclopenten-1'-yl)-2-nitroacetate (18d).

Viscous liquid; $^1$H NMR (CDCl$_3$, 250 MHz): δ 1.14 (dt, 3H, J=7.2, 2.0 Hz), 1.98 (s, 3H), 2.24 (m, 1H), 2.83 (m, 1H), 3.68 (m, 1H), 4.18 (dq, 2H, J=7.0, 1.5 Hz), 4.97 (dd, 1H, J=9.2, 5.5 Hz), 5.9 (m, 1H), 6.27 (dt, 1H, J=5.5, 2.0 Hz), 7.19-7.35 (m, 5H) ppm; $^{13}$C NMR (CDCl$_3$, 62.5 MHz): δ 13.9, 21.6, 41.9, 42.4, 44.4, 44.8, 63.2, 63.3, 81.9, 82.1, 86.3, 86.7, 90.5, 122.0, 128.2, 128.7, 131.8, 133.2, 133.7, 135.9, 136.2, 163.3, 169.1 ppm. HRESIMS calcd for C$_{19}$H$_{20}$NO$_6$ ([M+H]$^+$): 358.1291; found: 358.1294.

Example 26

Ethyl (2R/S,1'R,4'S)-2-(4'-acetoxy-2'-cyclopenten-1'-yl)-3-oxobutanoate (18f).

Viscous liquid; $^1$HNMR (CDCl$_3$, 250 MHz): δ 1.12 (t, 3H, J=7.2 Hz), 1.4 (t, 1H), 1.96 (s, 311), 2.18 (s, 3H), 2.9 (p, 1H, J=7.5 Hz), 3.33 (m, 2H), 4.03 (q, 2H, J=7.2 Hz), 5.5 (m, 1H), 5.81-5.82 (m, 2H) ppm; $^{13}$C NMR (CDCl$_3$, 62.5 MHz): δ 14.1, 21.2, 29.4, 29.7, 34.6, 34.7, 42.9, 43.0, 61.5, 61.6, 65.2, 65.3, 78.8, 78.9, 131.2, 131.3, 137.5, 137.6, 168.3, 170.7, 201.0, 201.9 ppm. HRESIMS calcd for C$_{13}$H$_{19}$O$_5$ ([M+H]$^+$): 255.1233; found: 255.1231.

Example 27

2-Phenylsulfonyl (2R/S,1'R,4'S)-2-(4'-acetoxy-2'-cyclopenten-1'-yl)-1-phenyl-ethanone (18i).

Viscous liquid; $^1$H NMR (CDCl$_3$, 250 MHz): δ 1.85-1.97 (s, 3H), 2.2-2.6 (m, 2H), 3.2-3.4 (m, 1H), 4.50 (dd, 1H, J=27.2, 10.2 Hz), 5.4-5.6 (m, 1H), 5.7-5.9 (dt, 1H, J=5.5, 2.2 Hz), 6.5 (m, 1H), 7.34-7.78 (m, 1OH) ppm; $^{13}$C NMR (CDCl$_3$, 62.5 MHz): δ 21.1, 21.2, 34.8, 35.6, 43.1, 43.8, 60.4, 65.1, 74.0, 74.2, 76.6, 128.8, 128.83, 128.89, 128.97, 129.92, 132.5, 134.1, 134.3, 134.4, 135.9, 136.6, 136.9, 137.1, 137.6, 170.4, 170.6, 192.5, 192.9 ppm. HRESIMS calcd for C$_{21}$H$_{21}$O$_5$S ([M+H]$^+$): 385.1100; found: 385.1103.

Example 28

Ethyl (2R/S,1'R,4'S)-2-(4'-acetoxy-2'-cyclopenten-1'-yl)-2-cyanoacetate (18n).

Viscous liquid; $^1$H NMR (CDCl$_3$, 250 MHz): δ 1.26 (t, 3H, J=7.0 Hz), 1.65 (m, 1H), 1.9 (s, 3H), 2.57 (p. 1H, J=6.5 Hz), 3.25 (m, 1H), 3.4-3.58 (2 doublets, (0.5×2H), J=6.5 Hz), 4.23 (q, 2H, J=7.0 Hz), 5.59 (m, 1H), 5.89-5.99 (m, 2H) ppm; $^{13}$C NMR (CDCl$_3$, 62.5 MHz): δ 14.0, 21.1, 33.8, 34.5, 42.7, 44.3, 62.9, 78.2, 78.3, 115.1, 133.5, 134.73, 165.1, 170.7, 170.8 ppm. HRESIMS calcd for C$_{12}$H$_{16}$NO$_4$ ([M+H]$^+$): 238.1079; found: 238.1080.

Example 29

Phenylsulfonyl (2R/S,1'R,4'S)-2-(4'-acetoxy-2'-cyclopenten-1'-yl)-2-acetomtrile (18o).

Viscous liquid; $^1$H NMR (CDCl$_3$, 250 MHz): δ 1.76-1.9 (m, 1H), 2.0 (s, 3H), 2.67 (m, 1H), 3.41 (m, 1H), 3.87-4.05 (2 doublets, 1H, J=6.25, 5.0 Hz), 5.55 (m, 1H), 5.91-6.05 (m, 2H), 7.56-7.98 (m, 5H) ppm; $^{13}$C NMR (CDCl$_3$, 62.5 MHz): δ 20.1, 32.8, 34.5, 40.5, 40.6, 60.5, 60.8, 76.9, 77.0, 111.8, 128.4, 128.5, 132.8, 133.0, 133.2, 133.5, 134.4, 134.9, 135.1, 169.7, 169.6 ppm. HRESIMS calcd for C$_{15}$H$_{16}$NO$_4$S ([M+H]$^+$): 306.0800; found: 306.0814.

Example 30

2-(4-Acetoxy-cyclopent-2-enyl)-malonic acid di-methyl ester (18p).

Viscous liquid; $^1$H NMR (CDCl$_3$, 250 MHz): δ 1.56 (dt, 1H, J=14.0, 4.5 Hz), 2.05 Cs, 3H), 2.54 (dt, 1H, J=14.0, 8.0 Hz), 3.33 (m, 2H), 3.77 (s, 6H), 5.6 (m, 1H), 5.88 (dt, 1H, J=5.7, 2.0 Hz), 6.00 (dt, 1H, J=5.7, 2.0 Hz) ppm; $^{13}$C NMR (CDCl$_3$, 100 MHz): δ 21.0, 34.5, 43.4, 52.3, 52.4, 56.7, 78.7, 131.3, 137.2, 168.4 (splits into 2), 170.6 ppm. HRESIMS calcd for C$_{12}$H$_{17}$O$_6$ ([M+H]$^+$): 257.1025; found: 257.1029.

Example 31

General Procedure for Preparation of Compounds 19a-m and 19p.

To a solution of 18a (70 mg, 0.272 mmol) in dry TFIF (10 ml) at room temperature were added potassium carbonate (37.6 mg, 0.272 mmol) and Pd(PPh3)4 (15 mg, 0.013 mmol). The reaction was allowed to stir for 12 h at 60 C and then vacuum filtered over Celite with subsequent concentration of the filtrate. The product was purified by wet column chromatography using ethyl acetate/hexane (1:2) to afford 19a using column chromatography as a yellow viscous liquid (45 mg, yield=85%).

Example 32

(1S,5S)-3-Aza-4-(ethoxycarbonyl)-2-oxabi-cyclo[3.3.0]oct-3,7-diene-3-oxide (19a).

Viscous liquid; $^1$H NMR (CDCl$_3$, 250 MHz): δ 1.29 (t, 3H, J=5.8 Hz), 2.63-2.78 (m, 2H), 4.17-4.28 (m, 3H, CH$_2$+H-4), 5.56-5.62 (m, 1H), 5.75-5.78 (m, 1H), 6.09-6.12 (m, 1H) ppm; $^{13}$C NMR (CDCl$_3$, 62.5 MHz): δ 14.0, 38.2, 44.6, 61.4, 84.2, 111.3, 127.7, 137.0, 158.9 ppm. HRESIMS calcd for C$_9$H$_{12}$NO$_4$ ([M+H]$^+$): 198.0766; found: 198.0762.

Example 33

(1S,5S)-3-Aza-4-(ethoxycarbonyl)-7-methyl-2-oxa-bicyclo[3.3.0]oct-3,7-diene-3-oxide (19b).

Viscous liquid; $^1$H NMR (CDCl$_3$, 400 MHz): δ 1.31 (t, 3H, J=6.8 Hz), 1.81 (s, 3H), 2.56 (d, 1H, J=17.6 Hz), 2.73 (dd, 1H, J=17.2, 8.0 Hz), 4.27 (m, 3H), 5.45 (s, 1H), 5.56 (d, 1H, J=8.8 Hz) ppm; $^{13}$C NMR (CDCl$_3$, 100 MHz): δ 14.4, 16.6, 42.6, 45.6, 61.8, 85.1, 112.1, 122.6, 148.5, 160.0 ppm. HRESIMS calcd for C$_{10}$H$_{14}$NO$_4$ ([M+H]$^+$): 212.0923; found: 212.0918.

Example 34

(1S,5S)-3-Aza-7-butyl-4-(ethoxycarbonyl)-2-oxabi-cyclo[3.3.0]oct-3,7-diene-3-oxide (19c).

Viscous liquid; $^1$H NMR (CDCl$_3$, 250 MHz): δ 0.79 (t, 3H, J=7.0 Hz), 1.20 (m, 5H, CH$_2$+CH$_3$), 1.33 (m, 2H), 2.07 (t, 2H, J=7.5 Hz), 2.53 (d, 1H, J=17.5 Hz), 2.75 (dd, 1H, J=16.0, 7.7 Hz), 4.24 (m, 3H), 5.43 (d, 1H, J=1.0 Hz), 5.33 (d, 1H, J=8.7 Hz); $^{13}$C NMR (CDCl$_3$, 62.5 MHz): δ 13.9, 13.9, 22.4, 29.6, 30.6, 42.5, 45.8, 61.5, 84.8, 112.3, 120.8, 150.3, 160.8 ppm. HRESIMS calcd for C$_{13}$H$_{20}$NO$_4$ ([M+H]$^+$): 254.1392; found: 254.1394.

Example 35

(1S,5S)-3-Aza-4-(ethoxycarbonyl)-7-phenyl-ethynyl-2-oxabicyclo[3.3.0]oct-3,7-diene-3-oxide (19d).

White solid: mp=72-74° C.; $^1$H NMR (CDCl$_3$, 250 MHz): δ 1.26 (t, 3H, J=7.0 Hz), 2.81-3.04 (m, 2H), 4.27 (m, 3H), 5.66 (d, 1H, J=9.0 Hz), 6.01 (d, 1H, J=2.0 Hz), 7.25-7.40 (m, 5H, Ph) ppm; $^{13}$C NMR (CDCl$_3$, 62.5 MHz): δ 14.2, 41.8, 45.0, 61.8, 83.7, 83.9, 95.5, 110.9, 122.1, 128.4, 129.0, 131.0, 131.4, 131.7, 159.0 ppm; MS(ESI) m/z=298.1 [M+H]$^+$. HRESIMS calcd for C$_{17}$H$_{16}$NO$_4$ ([M+H]$^+$): 298.1079; found: 298.1072.

X-ray crystallographic data for 19d.

For the crystal of 19d, four molecules were found in each unit cell. The compound crystallized in an orthorhombic space, group P2(1)2(1)2(1), with cell dimensions a=6.630(4) Å, b=10.067(6) Å, c=21.631(11) Å. A total of 3479 unique reflection data were obtained to give a final R indices [1>2σ(I)] of R1=0.0626, wR2=0.1308 and R indices (all data) R1=0.0824, wR2=0.1444.

TABLE 2

| | |
|---|---|
| Identification code | kb0825 |
| Empirical formula | C$_{17}$H$_{15}$NO$_4$ |
| Formula weight | 297.30 |
| Temperature | 100(2) K |
| Wavelength | 0.71073 Å |
| Crystal system | Orthorhombic |
| Space group | P2(1)2(1)2(1) |
| Unit cell dimensions | a = 6.630(4) Å ☐ = 90°. |
| | b = 10.067(6) Å ☐ = 90°. |
| | c = 21.631(11) Å ☐ = 90°. |
| Volume | 1443.7(15) Å$^3$ |
| Z | 4 |
| Density (calculated) | 1.368 Mg/m$^3$ |
| Absorption coefficient | 0.098 mm$^{-1}$ |
| F(000) | 624 |
| Crystal size | 0.30 × 0.07 × 0.06 mm$^3$ |
| Theta range for data collection | 1.88 to 25.01°. |
| Index ranges | −7 <= h <= 6, −11 <= k <= 8, −14 <= 1 <= 20 |
| Reflections collected | 3479 |
| Independent reflections | 2176 [R(int) = 0.0437] |
| Completeness to theta = 25.01° | 87.8% |
| Absorption correction | SADABS |
| Max. and min. transmission | 1.000 and 0.598 |
| Refinement method | Full-matrix least-squares on F$^2$ |
| Data/restraints/parameters | 2176/0/206 |
| Goodness-of-fit on F$^2$ | 1.009 |
| Final R indices [I > 2sigma(I)] | R1 = 0.0626, wR2 = 0.1308 |
| R indices (all data) | R1 = 0.0824, wR2 = 0.1444 |
| Absolute structure parameter | 0(3) |
| Largest diff. peak and hole | 0.251 and −0.201e, Å$^{-3}$ |

Example 36

(1S,5S)-3-Aza-4-(ethoxycarbonyl)-7-trimethylsilanylethynyl-2-oxabicyclo [3.3.0]oct-3,7-diene-3-oxide (19e).

$^1$H NMR (CDCl$_3$, 250 MHz): δ 0.10 (s, 9H), 1.25 (t, 3H, J=7.0 Hz), 2.85-3.09 (m, 2H), 4.20 (m, 3H), 5.70 (d, 1H, J=8.7 Hz), 6.05 (d, 1H, 0.1=2.0 Hz) ppm; $^{13}$C NMR (CDCl$_3$, 62.5 MHz): δ 0.5, 14.3, 40.9, 44.5, 62.0, 82.7, 99.4, 102.0, 111.2, 128.1, 136.2, 160.0 ppm; MS(ESI) m/z=294.1 [M+H]$^+$. HRESIMS calcd for C$_{14}$H$_{20}$NO$_4$Si ([M+H]$^+$): 294.1162; found: 294.1165.

Example 37

(1S,5S)-4-(Ethoxycarbonyl)-3-methyl-2-oxabi-cyclo[3.3.0]oct-3,7-diene (19f).

Viscous liquid; $^1$H NMR (CDCl$_3$, 250 MHz): δ 1.20 (t, 3H, J=7.2 Hz), 2.09 (s, 3H), 2.3 (m, 1H), 2.6 (m, 1H), 3.7 (t, 1H, J=8.4 Hz), 4.10 (q, 2H, J=6.8 Hz), 5.53 (d, 1H, J=9.2 Hz), 5.7. (br s, 1H), 5.9 (br s, 1H) ppm; $^{13}$C NMR (CDCl$_3$, 62.5 MHz): δ 14.5, 14.6, 40.1, 43.9, 59.5, 91.9, 106.6, 128.5, 137.0, 166.4, 167.1 ppm. HRESIMS calcd for C$_{11}$H$_{15}$O$_3$ ([M+H]$^+$): 195.1021; found: 195.1018.

Example 38

(1S,5S)-4-(Ethoxycarbonyl)-3,7-dimethyl-2-oxa-cyclo[3.3.0]oct-3,7-diene (19g).

Viscous liquid; $^1$H NMR (CDCl$_3$, 250 MHz): δ 1.21 (t, 3H, J=7.0 Hz), 1.71 (m, 3H), 2.09 (d, 3H, J=1.2 Hz), 2.27-2.34 (m, 1H), 2.51-2.55 (m, 1H), 3.70 (dt, 1H, J=7.7, 1.0 Hz), 4.1 (m, 2H), 5.34 (m, 1H), 5.46 (d, 1H, J=8.8 Hz) ppm; $^{13}$C NMR (CDCl$_3$, 62.5 MHz): δ 14.42, 14.48, 16.5, 44.1, 44.6, 59.2, 92.3, 106.5, 123.0, 147.8, 166.3, 167.2 ppm. HRESIMS calcd for C$_{12}$H$_{17}$O$_3$ ([M+H]$^+$): 209.1178; found: 209.1181.

Example 39

(1S,5S)-7-Butyl-4-(ethoxycarbonyl)-3-methyl-2-oxabicyclo[3.3.0]oct-3,7-diene (19h).

Viscous liquid; $^1$H NMR (CDCl$_3$, 250 MHz): δ 0.78 (t, 3H, J=7.0 Hz), 1.21 (m, 5H), 1.34 (m, 2H), 2.04 (m, 5H, CH$_3$+CH$_2$), 2.33 (dd, 1H, J=14.0, 1.0 Hz), 2.53 (dd, 1H, J=14.0, 8.0 Hz), 3.72 (m, 1H), 4.07 (m, 2H), 5.34 (d, 1H, J=1.25 Hz), 5.47 (d, 1H, J=9.0 Hz) ppm; $^{13}$C NMR (CDCl$_3$, 62.5 MHz): δ 13.8, 14.45, 14.49, 22.5, 29.6, 30.7, 42.5, 44.1, 59.2, 92.2, 106.5, 121.5, 152.2, 166.4, 167.2 ppm. HRESIMS calcd for $C_{15}H_{23}O_3$ ([M+H]$^+$): 251.1647; found: 251.1645.

Example 40

(1S,5S)-3-Phenyl-4-(phenylsulfonyl)-2-oxabi-cyclo[3.3.O] oct-3,7-diene (19i).

Viscous liquid; $^1$H NMR (CDCl$_3$, 250 MHz): δ 2.73 (dt, 1H, J=7.2, 2.2 Hz), 2.85 (p, 1H, J=2.2 Hz), 3.82 (dt, 1H, J=7.7, 5.2 Hz), 5.64 (doublet of p, 1H, J=7.2, 1.2 Hz), 5.74 (dq, 1H, J=5.7, 2.2 Hz), 6.06 (dt, 1H, J=5.7, 1.2 Hz), 7.18-7.6 (m, IOH) ppm; $^{13}$C NMR (CDCl$_3$, 62.5 MHz): δ 40.1, 46.4, 91.9, 114.4, 127.0, 127.4, 127.9, 128.7, 128.8, 129.4, 130.7, 132.6, 137.2, 142.2, 163.9, 192.3 ppm. HRESIMS calcd for $C_{19}H_{17}O_3S$ ([M+H]$^+$): 325.0898; found: 325.0892.

Example 41

(1S,5S)-7-Methyl-3-phenyl-4-(phenylsulfonyl)-2-oxabicyclo[3.3.O] oct-3,7-diene (19j).

Viscous liquid; $^1$H NMR (CDCl$_3$, 250 MHz): δ 1.76 (s, 3H), 2.58-2.90 (m, 2H), 3.84 (dt, 1H, J=7.7, 2.2 Hz), 5.41 (t, 1H, J=2.0 Hz), 5.62 (d, 1H, J=9.0 Hz), 7.19-7.60 (m, 10H, PhSO$_2$+COPh) ppm; $^{13}$C NMR (CDCl$_3$, 62.5 MHz): δ 15.5, 43.2, 46.2, 91.6, 113.3, 121.5, 125.9, 126.6, 127.7, 128.0, 128.4, 129.6, 131.5, 141.3, 147.3, 163.1 ppm. HRESIMS calcd for $C_{20}H_{19}O_3S$ ([M+H]$^+$): 339.1055; found: 339.1050.

Example 42

(1S,5S)-7-Butyl-3-phenyl-4-(phenylsulfonyl)-2-oxabicyclo [3.3.O] oct-3,7-diene (19k).

Viscous liquid; $^1$H NMR (CDCl$_3$, 250 MHz): δ 0.80 (t, 3H, J=7.2 Hz), 1.19 (m, 2H), 1.31 (m, 2H), 2.05 (t, 2H, J=7.5 Hz), 2.58-2.90 (m, 2H), 3.80 (dt, 1H, J=7.7, 2.2 Hz), 5.40 (d, 1H, J=2.0 Hz), 5.60 (d, IH, J=9.2 Hz), 7.19-7.60 (m, 10H, PhSO$_2$+COPh) ppm; $^{13}$C NMR (CDCl$_3$, 62.5 MHz): δ 13.9, 22.4, 29.5, 30.6, 42.5, 46.7, 92.4, 114.3, 121.1, 126.9, 127.7, 128.7, 129.1, 129.4, 130.6, 132.5, 142.4, 152.7, 164.1 ppm. HRESIMS calcd for $C_{23}H_{25}O_3S$ ([M+H]$^+$): 381.1524; found: 381.1522.

Example 43

(1S,5S)-3-Phenyl-7-phenylethynyl-4-(phenylsul-fonyl)-2oxabicyclo [3.3.0] oct-3,7-diene (19l).

Viscous liquid; $^1$H NMR (CDCl$_3$, 250 MHz): δ 2.89-3.17 (m, 2H), 3.94 (dt, 1H, J=8.2, 2.2 Hz), 5.70 (d, 1H, J=9.0 Hz), 6.00 (d, 1H, J=1.7 Hz), 7.26-7.61 (m, 15H); $^{13}$C NMR (CDCl$_3$, 62.5MHz): δ 43.7, 46.6, 84.5, 91.4, 94.8, 114.3, 122.5, 127.0, 127.7, 128.4, 128.6, 128.8, 129.4, 130.8, 131.0, 131.7, 131.9, 132.0, 132.7, 142.1, 164.2 ppm. HRESIMS calcd for $C_{27}H_{21}O_3S$ ([M+H]$^+$): 425.1211; found: 425.1203.

Example 44

(1S,5S)-3-Phenyl-4-(phenylsulfonyl)-7-trimethyl-silanyl-2oxabicyclo [3.3.0]oct-3,7-diene (19m).

Viscous liquid; $^1$H NMR (CDCl$_3$, 250 MHz): δ 0.14 (s, 9H), 2.85-3.05 (m, 2H), 3.99 (dt, 1H, J=8.5, 2.0 Hz), 5.72 (d, 1H, J=9.0 Hz), 6.10 (d, 1H, J=1.7 Hz), 7.26-7.65 (m, 10H, PhSO$_2$+COPh) ppm; $^{13}$C NMR (CDCl$_3$, 62.5 MHz): δ 0.5, 43.5, 46.7, 90.5, 98.0, 102.1, 114.2, 122.7, 127.5, 128.7, 129.0, 129.6, 131.4, 133.0, 134.4, 165.0 ppm. HRESIMS calcd for $C_{24}H_{25}O_3SSi$ ([M+H]$^+$): 421.1294; found: 421.1288.

Example 45

2-Cyclopent-2-enylidene-malonic acid dimethyl ester (19p).

Viscous liquid; $^1$H NMR (CDCl$_3$, 250 MHz): δ 2.58 (m, 2H), 2.90 (m, 2H), 3.70 (s, 3H), 3.73 (s, 3H), 6.76 (s, 2H) ppm; $^{13}$C NMR (CDCl$_3$, 62.5 MHz): δ 31.0, 32.9, 51.8, 52.0, 115.3, 132.4, 152.4, 166.2, 166.6, 168.3 ppm. HRESIMS calcd for $C_{10}H_{13}O_4$ ([M+H]$^+$): 197.0814; found: 197.0812.

Example 46

Antiviral Screening

Madin Darby canine kidney (MDCK) cells were obtained from American Type Culture Collection (Manassas, Va., CCL-34, passage 55) and grown in Eagle minimum essential medium (MEM, Invitrogen) with 10% reconstituted fetal calf serum (HyClone III). The cells were trypsinized, then resuspended at 3×10$^5$ cells/mL in high glucose DMEM with phenol red for Primary screening or DMEM, high glucose without phenol red for Secondary screening, supplemented with gentamicin and 0.5% BSA (instead than HyClone III), for all subsequent steps. Cells were plated manually and incubated at 37° C. and 5.0% CO$_2$ for 24 h prior to virus addition.

Influenza strains A/PR8/38 (H1N1), A/Wyoming/3/2003 (H2N3) and B/Lee/40 were grown in MDCK cells. The supernatant from infected MDCK cells was serially diluted and used for isolation of a single plaque. A single plaque from second round of plaque purification was selected and resuspended in serum-free Dulbecco's modified Eagle's medium (DMEM, Invitrogen, Carlsbad, Calif.) containing 0.35% bovine serum albumin (BSA, Invitrogen, Fraction V). The plaque-purified virus was used to inoculate three T150 flasks containing MDCK cells (see below) at a multiplicity of infection of 0.001 PFU/cell. The supernatant was collected 72h post infection, aliquoted and stored at −80° C. until needed.

Protocol to Determine Multiplicity of Infection.

Ninety six well plates were plated with MDCK cells at a density of 1.5×10$^4$ per well (3×10$^5$ cells/mL, 50 µl of cells/well). Twenty four hours after plating, the media was replaced with MEM containing 50 µl of N-acetyl trypsin (5 µg/mL, diluted in assay media). Amplified influenza virus was diluted 100-fold in assay media containing 2.5 µg/mL N-acetyl trypsin, then added to the first column of the plate and successively serially diluted across the remaining plate columns. Fresh pipette tips were used for each dilution to avoid virus carry over to subsequent columns, and the cells in the last plate column is left uninfected as controls. The plates are incubated at 37° C. with 5.0% CO$_2$ for 72 h. Control wells containing medium without cells were used to obtain a value for background absorbance. After incubation at 37° C. for 72 h the plates were visually scored as previously indicated and analyzed using CellTiter 96 Aqueous One Solution as indicated above. Three replicate plates were analyzed; individual plates were averaged to establish the TCID$_{50}$ and determined the virus dilution needed to obtain the appropriate MOI for each viral strain.

Identification of Drug Candidates with Anti-Influenza Activity.

Primary screening of synthesized compounds for antiviral activity against influenza A/WY/03/2003 (H3N2) using light microscopy scoring of cytopathic effect (CPE) and colorimetric quantification of cell viability.

Primary Antiviral Efficacy Screening

Microscopic evaluation of CPE.

Primary screening was performed using influenza virus strain A/Wyoming/03/2003 (H3N2). The primary screening was based on the determination of reduction in cytophatic effect (CPE) evaluated using visual scoring. Each well was observed at a magnification of 40× using an inverted microscope. Complete CPE was recorded with two plus signs (++), partial CPE (some cells appear without signs of CPE are recorded with one plus sign (+), complete protection (no signs of CPE are observable are recorded with a minus sign (−).

Quantitative cell viability assay.

Cell viability was quantified using a commercially available MTT cell viability test (CellTiter 96 Aqueous One Solution, Promega). This colorimetric method was used in the secondary screening for the determination of dose response and cytotoxic effects. This approach has been previously validated and confirmed to be statistically comparable to other methods (Chotpitayasunondh, T., et al. 2005. Human disease from influenza A (H5N1), Thailand, 2004. Emerg. Infect. Dis. 11:201-209; Smee, D. F., et al. 2002. Comparison of colorimetric, fluorometric, and visual methods for determining anti-influenza (H1N1 and H3N2) virus activities and toxicities of compounds. Journal of Virological Methods 106: 71-79). A single-dose (10 μg/mL), single-well per compound was tested in 96-well plates. Briefly, 50 μl of media (DMEM/F12(1:1), Hyclone SH30272.01, supplemented with 0.35% BSA and 2.5 μg/mL of N-Acetyl trypsin, and sodium pyruvate) was added to each well, followed by addition of 20 μl of a compound of interest (60 μg/mL) to each test well. A/WY/03/2003 (H3N2) influenza virus was added in 50 μl volume at a dilution that produces CPE in 99% of the wells corresponding to approximately 40 $TCID_{50}$ ($1\times10^{-4}$ dilution of the virus stock of $7.8\times10^6 TCID_{50}$/mL). Subsequently, 50 μl of the above media containing 16,000 MDCK (NBL-1, ATCC Number CCL-22) was added to each well. The final volume in each well was 120 μl. Plates were then incubated at 37° C., in 5% $CO_2$ for 72 h. The preparation of the master and mother plates and the handling of media, compound, virus and cells was performed employing a Biomek 3000 and BC NX robots placed inside a biosafety level 2 cabinet. Experimental controls in each plate included uninfected cells, infected cells and ribavirin at a concentration of 5 μg/mL. Reduction of CPE was qualitatively evaluated by direct observation of cytopathic effect using an inverted light microscope. After the visual evaluation 20 μl of CellTiter 96 Aqueous-One reagent was added to each well, mixed by vortexing and incubated at 37° C. for 2 h. Optical density was measured at absorbance of 490 using a BioTek Synergy HT plate reader. Percentage of protection was calculated using the following formula: (1-(($\mu_c$-OD of Sample)/($\mu_c$-$\mu_v$)))*100; where $\mu_c$=mean optical density (OD) value of the uninfected cells, $\mu_v$=mean OD value of the infected cells.

After measurement of the cell viability, the plates were stained using a 2.5% crystal violet solution in PBS containing 4% formaldehyde. The purpose of performing this staining is to create a permanent record of the plates and to corroborate the cell viability assay with the visual scoring of CPE. To confirm the results of primary screening, compound displaying ≧50% protection against CPE at 100 μg/mL, were re-tested in triplicate using the primary screening protocol.

Figures 17, 18:
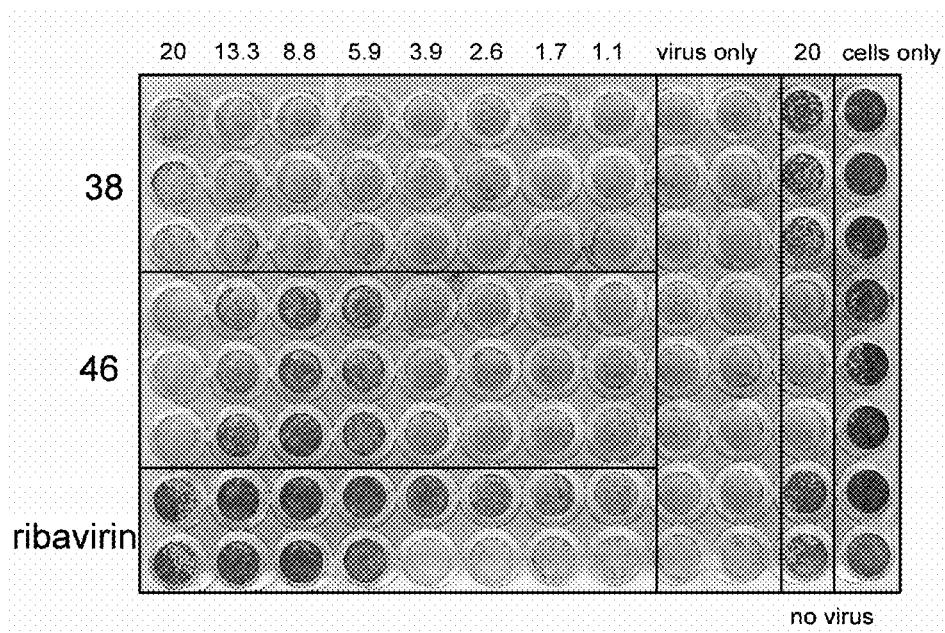
FIG. 17 is a microscopic evaluation of the cells, showing visual scoring for cytophatic effect. Wells A-C12 contained uninfected control, D-E12 contained 5 g/mL ribavirin, and F-H12 were the virus infected wells. It is important to indicate that the crystal violet staining is only used as an additional indicator of cell protection and not as a quantitative measure of cell protection
FIG. 18 is a photograph of a screening using compound 38, from well F5, and compound 46, from well F6. The compound was serially diluted ⅔. Compound 46 was ethyl (2r/S, 1'R,4'S)-2-(4'-hydroxy-2'-cyclopenten-1'-yl)-2-nitroacetate.

In FIGS. 16 and 17, the compound in position F6 did not present complete CPE when observed under the microscope and the cell viability assay indicated 75% protection at 100 μg/mL. Wells A-C12 contained uninfected control, D-E12 contained control drug ribavirin at 5 μg/mL and F-H12 were the virus-infected control. It is important to indicate that the crystal violet staining is only used as an additional indicator of cell protection and not as a quantitative measure of cell protection.

Secondary Antiviral Efficacy Screening

Compound 46, ethyl (2r/S, 1'R,4'S)-2-(4'-hydroxy-2'-cyclopenten-1'-yl)-2-nitroacetate (EHCN) was partially characterized and evaluated using a series of eight ⅔ serial dilutions to determine whether this compound resulted in protection against influenza virus infections in a dose dependant manner in triplicate. The resulting concentrations in μg/mL were 20, 13.3, 8.8, 5.9, 3.9, 2.6, 1.7, and 1.1. Percentage of protection was quantified using the previously mentioned cell viability assay. 38 is an inactive compound. Ribavirin was used as drug control at concentrations 10 to 1.5 μg/mL. FIG. 18 presents the results of one of two independent this evaluations. The $EC_{50}$ of EHCN against A/WY/03/2003 was estimated at 4.5 ug/ml.

Figure 19:
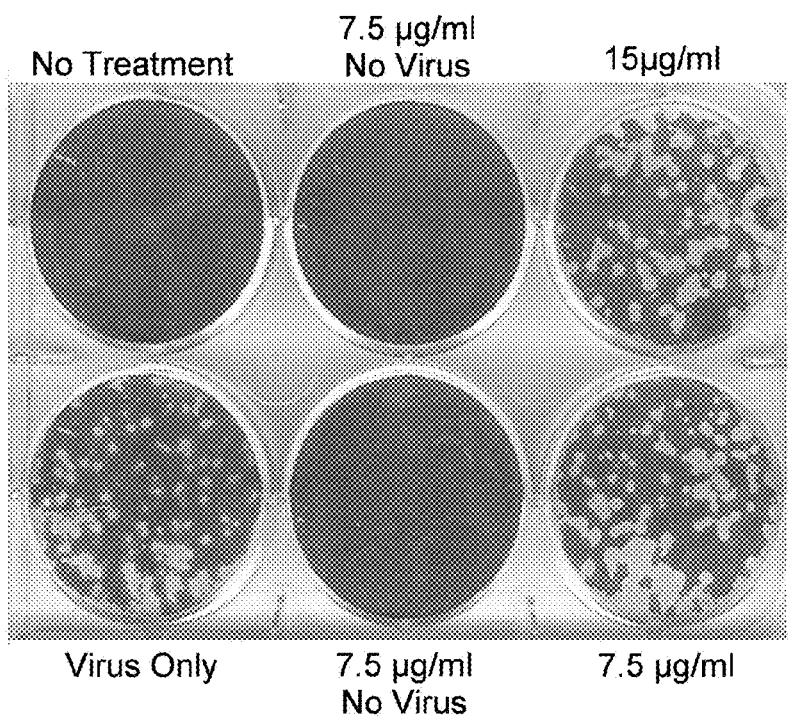
FIGS. 19(a)-(b) are photographs of screenings of plaque assays to determine the inhibitory effect on viral progeny. (A) Testing of compound 38 under depicted conditions. (B) Testing of compound 46 under depicted conditions.
Figure 19:
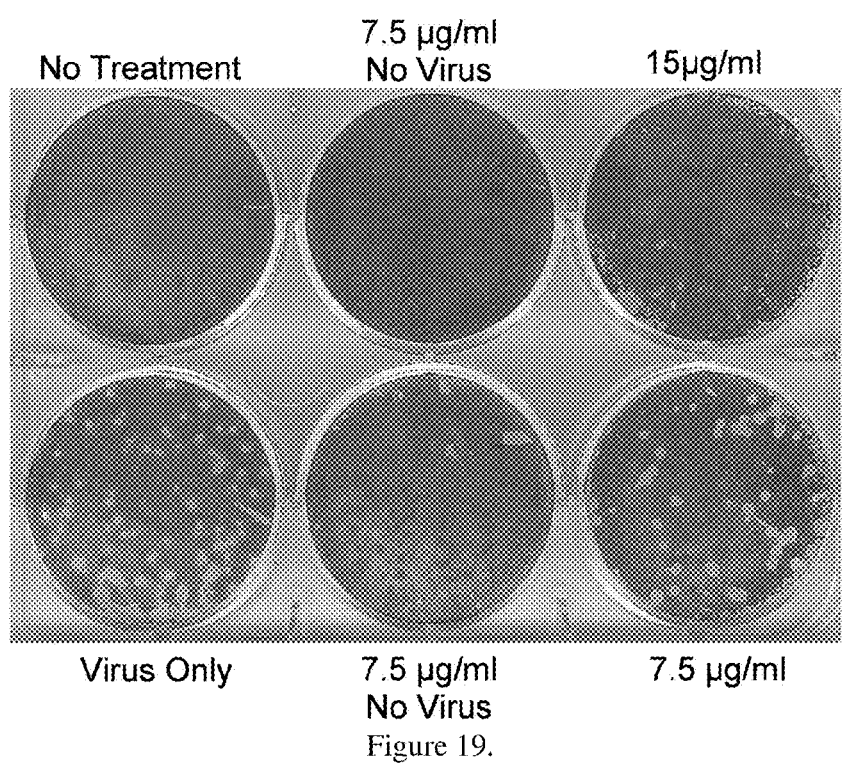

The ability of this compound was then tested for growth inhibition of the virus in multiple rounds of replication using plaque reduction assay. For these experiments 12-well plates containing 80% confluent MDCK cells monolayer were inoculated with the 150 pfu and incubated for 1 h at 4° C. before adding a semisolid agar overlay containing the indicated μg/mL of EHCN (compound 46) and compound 38, seen in FIGS. 19(a) and (b). The plates were incubated at 37° C. for 72 h and then stained using crystal violet/formalin solution. EHCN was used at 15 and 7.5 μg/ml, seen in FIG. 19(b), which is consistent with the results obtained in earlier experiments. EHCN induced the formation of fewer and smaller plaques than the untreated wells. In contrast, compound 38 did not present antiviral activity.

This selectivity screen has a number of advantages, primarily in identifying anti-influenza-selective. Furthermore, the proposed cell based screen offers the additional advantage of evaluating inhibitory activity of multiple molecular targets and viral stages of replication and cytotoxicity of compounds simultaneously (Noah, J. W., et al. 2006. A cell-based luminescence assay is effective for high-throughput screening of potential influenza antivirals. Antiviral. Res. 73:50-59).

The virus progeny of wells exhibiting drug-induced CPE protection were analyzed to quantitatively determine the reduction in virus progeny after a single replication cycle using $TCID_{50}$. Forty-eight well plates containing 80% confluent MDCK cell monolayers were infected with 40 $TCID_{50}$ of influenza virus in 600 μl of media containing N-Acetyl trypsin and BSA as previously indicated, and incubated at 37° C. for 24 h. The plates were freeze-thawed three times and the media-cell suspension transferred to microcentrifuge tubes to pellet the cell debris. One hundred microliters of supernatant were diluted at 1/100. This dilution was added to the first eight wells of a 96-well tissue culture plate containing MDCK cells as described in previous sections. Subsequently the virus was diluted in a 10-fold serial dilution and the CPE visually scored and quantified using the colorimetric cell viability method described in section C1.2.

Cytotoxicity Evaluation.

The selectivity of active compounds was evaluated using the same plate configuration described in above, however cell line A549 was used in addition to MDCK at lower density since the latter are reportedly less susceptible to cytotoxic effect (Gebre-Mariam, T., et al. 2006. Antiviral activities of some Ethiopian medicinal plants used for the treatment of dermatological disorders. J. Ethnopharmacol. 104:182-187). The cytotoxic concentration 50% ($CC_{50}$) was evaluated after the primary screen. The cells were plated at lower density (50% confluency) to aid in the evaluation of potential cytostatic effect. Ribavirin at 10 μg/mL and amantadine at 120 μg/mL were used as cytostatic and cytotoxic control drugs. The quantification of cell viability was measured using the cell viability assay previously described in the primary screening (CellTiter 96 Aqueous-One, Promega).

Specificity was tested by evaluating the effect on the growth of unrelated viruses (cytopathic bovine viral diarrhea virus). Studying the mode of action (MOA) of active compounds was accomplished by analyzing the results of the primary and secondary screening (Single vs. multiple rounds of replication and effect on progeny growth, early and late stage of infection).

After performing the primary screening in triplicate, compounds that exhibited significant inhibitory activity, defined as ≧50% inhibition of CPE at 10 µg/mL, including confirmation of activity observed during the primary screen were subjected to secondary screening. An expanded range of compound concentrations (dose response), plaque inhibition assay, one step growth inhibition and testing of additional influenza viruses such as [A/NWS/33 (H1N1), and B/Lee/40 and low pathogenic avian influenza A/TY/WI/68 (H5N9) and A/TY/UT/24721-10/95 (H7N3)] were used. During the secondary screening cytotoxicity was evaluated in mammalian cells.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

While there has been described and illustrated specific embodiments of a method of treating neurodegenerative disease, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method of treating a cell infected with Orthomyxoviridae virus, comprising the step of:
    contacting the cell infected with Orthomyxoviridae virus with a therapeutically effective amount of a monocyclic cyclopentene compound;
    where the monocyclic cyclopentene compound is ethyl-(2R/S, 1'R,4'S)-2-(4'-hydroxy-2'-cyclopenten-1'-yl)-2-nitroacetate.

2. The method of claim 1, wherein the Orthomyxoviridae virus is selected from the group consisting of type A and type B.

3. The method of claim 1, wherein the ethyl-(2R/S, 1'R, 4'S)-2-(4'-hydroxy-2'-cyclopenten-1'-yl)-2-nitroacetate is administered between 1.1 and 20 µg/ml.

4. The method of claim 3, wherein the ethyl-(2R/S, 1'R, 4'S)-2-(4'-hydroxy-2'-cyclopenten-1'-yl)-2-nitroacetate is administered between 3.9 and 13.3 µg/ml.

5. The method of claim 3, wherein the ethyl-(2R/S, 1'R, 4'S)-2-(4'-hydroxy-2'-cyclopenten-1'-yl)-2-nitroacetate is administered at 5 µg/ml.

6. A method of treating Orthomyxoviridae infection in a patient in need thereof, comprising the step of:
    administering a therapeutically effective amount of a ethyl-(2R/S, 1'R,4'S)-2-(4'-hydroxy-2'-cyclopenten-1'-yl)-2-nitroacetate to the patient infected with Orthomyxoviridae virus.

7. The method of claim 6, wherein the Orthomyxoviridae virus is selected from the group consisting of type A and type B.

8. The method of claim 6, wherein the ethyl-(2R/S, 1'R, 4'S)-2-(4'-hydroxy-2'-cyclopenten-1'-yl)-2-nitroacetate is administered between 1.1 and 20 µg/ml.

9. The method of claim 8, wherein the ethyl-(2R/S, 1'R, 4'S)-2-(4'-hydroxy-2'-cyclopenten-1'-yl)-2-nitroacetate is administered between 3.9 and 13.3 µg/ml.

10. The method of claim 9, wherein the ethyl-(2R/S, 1'R, 4'S)-2-(4'-hydroxy-2'-cyclopenten-1'-yl)-2-nitroacetate is administered at 5 µg/ml.

11. The method of claim 3, wherein the ethyl-(2R/S, 1'R, 4'S)-2-(4'-hydroxy-2'-cyclopenten-1'-yl)-2-nitroacetate is administered at 4.5 µg/ml.

12. The method of claim 2, wherein the Orthomyxoviridae type A subtype is selected from the group consisting of H1N1, H3N2, H5N9, and H7N3.

13. The method of claim 9, wherein the ethyl-(2R/S, 1'R, 4'S)-2-(4'-hydroxy-2'-cyclopenten-1'-yl)-2-nitroacetate is administered at 4.5 µg/ml.

14. The method of claim 7, wherein the Orthomyxoviridae type A subtype is selected from the group consisting of H1N1, H3N2, H5N9, and H7N3.

* * * * *